US012567185B2

(12) United States Patent
Dickie et al.

(10) Patent No.: US 12,567,185 B2
(45) Date of Patent: Mar. 3, 2026

(54) METHOD AND SYSTEM OF CREATING AND DISPLAYING A VISUALLY DISTINCT RENDERING OF AN ULTRASOUND IMAGE

(71) Applicant: Clarius Mobile Health Corp., Vancouver (CA)

(72) Inventors: Kris Dickie, Vancouver (CA); Laurent Pelissier, North Vancouver (CA); Benjamin Eric Kerby, Richmond (CA); Nishant Uniyal, Vancouver (CA); Matt Potma, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 159 days.

(21) Appl. No.: 18/387,825

(22) Filed: Nov. 7, 2023

(65) Prior Publication Data

US 2025/0148669 A1    May 8, 2025

(51) Int. Cl.
  *G06T 11/60* (2026.01)
  *A61B 8/00* (2006.01)
    (Continued)

(52) U.S. Cl.
  CPC ................ *G06T 11/60* (2013.01); *G06T 7/12* (2017.01); *G06T 7/251* (2017.01); *A61B 8/461* (2013.01);
    (Continued)

(58) Field of Classification Search
  CPC ......... A61B 8/461; A61B 8/463; G06T 11/60; G06T 2207/10132; G06T 2207/20081;
    (Continued)

(56) References Cited

U.S. PATENT DOCUMENTS 8,396,268 B2    3/2013  Zabair et al.
8,469,890 B2    6/2013  Langeland et al.
    (Continued)

OTHER PUBLICATIONS

Eramian, M. G., Adams, G. P., & Pierson, R. A. (2007). Enhancing ultrasound texture differences for developing an in vivo 'virtual histology' approach to bovine ovarian imaging. Reproduction, fertility, and development, 19(8), 910-924. https://doi.org/10.1071/rd06167.
    (Continued)

*Primary Examiner* — Ming Wu
(74) *Attorney, Agent, or Firm* — Julian Ho; Susan Ben-Oliel

(57) ABSTRACT

A method of creating and displaying a visually distinct rendering of an ultrasound image, acquired from an ultrasound scanner, comprises displaying, on a screen that is communicatively connected to the ultrasound scanner, an ultrasound image feed comprising ultrasound image frames, deploying an AI model to execute on a computing device communicably connected to the ultrasound scanner, wherein the AI model is trained so that when the AI model is deployed, the computing device identifies and segments boundaries of a feature or features, in whole or part, acquiring, at the computing device, a new ultrasound image during ultrasound scanning, processing, using the AI model, the new ultrasound image to identify and segment boundaries of a single feature or two or more features, in whole or part, on the new ultrasound image, thereby creating a single segmented boundary feature or two or more segmented boundary features, applying a graphic onto the single segmented boundary feature or the at least two segmented boundary features, thereby forming a graphic feature image and generating an output image, on the screen, comprising the graphic feature image.

20 Claims, 16 Drawing Sheets
(10 of 16 Drawing Sheet(s) Filed in Color)

600

(51) Int. Cl.
  *G06T 7/12*       (2017.01)
  *G06T 7/246*      (2017.01)

(52) U.S. Cl.
  CPC .............. *G06T 2207/10132* (2013.01); *G06T 2207/20081* (2013.01); *G06T 2207/20221* (2013.01); *G06T 2207/30004* (2013.01)

(58) Field of Classification Search
  CPC . G06T 2207/20084; G06T 2207/20221; G06T 2207/30004; G06T 7/12; G06T 7/251
  See application file for complete search history.

(56)        References Cited

U.S. PATENT DOCUMENTS

| | | | |
|---|---|---|---|
| 9,888,178 | B2 | 2/2018 | Sornes |
| 10,489,969 | B2 | 11/2019 | Buckton et al. |
| 11,094,138 | B2 | 8/2021 | Canfield et al. |
| 2010/0123714 | A1 | 5/2010 | Langeland et al. |
| 2019/0156526 | A1 | 5/2019 | Liu et al. |
| 2019/0261942 | A1* | 8/2019 | Yang .................... A61B 8/5207 |
| 2019/0392944 | A1* | 12/2019 | Samset .................. G16H 30/40 |
| 2022/0392065 | A1* | 12/2022 | Min ..................... A61B 6/5205 |
| 2022/0409181 | A1* | 12/2022 | Dickie ................... A61B 8/085 |

OTHER PUBLICATIONS

Pal, Prasanta; Vago, David R.; Ghosh, Amardip; Brewer, Judson (2021): Aestheticization of Ultrasound Images. TechRxiv. Preprint. https://doi.org/10.36227/techrxiv.16543488.v1.

Illanes A, Esmaeili N, Poudel P, Balakrishnan S, Friebe M (2019) Parametrical modelling for texture characterization—A novel approach applied to ultrasound thyroid segmentation. PLoS One 14(1): e0211215. https://doi.org/10.1371/journal.pone.0211215.

Sumanaweera, Thilaka. (2004) Chapter 40. Applying Real-Time Shading to 3D Ultrasound Visualization. GPU Gems Nvidia Corporation. Siemens Medical Solutions USA, Inc. https://developer.nvidia.com/gpugems/gpugems/part-vi-beyond-triangles/chapter-40-applying-real-time-shading-3d-ultrasound.

Madasu, V. K.; Yarlagadda, P. (2007) An in-depth comparison of four texture segmentation methods. IEEE Explore. DOI:10.1109/DICTA.2007.4426820.

Attique M, Gilanie G, Hafeez-Ullah, Mehmood MS, Naweed MS, et al. (2012) Colorization and Automated Segmentation of Human T2 MR Brain Images for Characterization of Soft Tissues. PLoS One 7(3): e33616. doi:10.1371/journal.pone.0033616.

Garcia, D.; Lantelme, P.; Saloux, E. (2018) Introduction to speckle training in cardiac ultrasound imaging. In book: Handbook of Speckle Filtering and Tracking in Cardiovascular Ultrasound Imaging and Video; Chapter 26. The Institution of Engineering and Technology. DOI:10.1049/PBHE013E_ch26.

Fabiani, I., Pugliese, N. R., Santini, V., Conte, L., & Di Bello, V. (2016). Speckle-Tracking Imaging, Principles and Clinical Applications: A Review for Clinical Cardiologists. InTech. doi: 10.5772/64261. https://www.intechopen.com/chapters/51931.

* cited by examiner

100

ACQUIRE NEW IMAGING FRAME — 102

PRE-PROCESS / ADJUST RESOLUTION — 103

PROCESS IMAGE WITH AI MODEL — 104

IDENTIFY / SEGMENT BOUNDARIES OF A SINGLE OR TWO OR MORE FEATURES — 106

APPLY GRAPHICS ONTO THE SINGLE SEGMENTED BOUNDARY FEATURE OR TWO OR MORE SEGMENTED BOUNDARY FEATURES — 108

DISPLAY OUTPUT (GRAPHIC FEATURE IMAGE) — 110

REPEAT STEPS 102-110 FOR ADDITIONAL IMAGES — 112

200
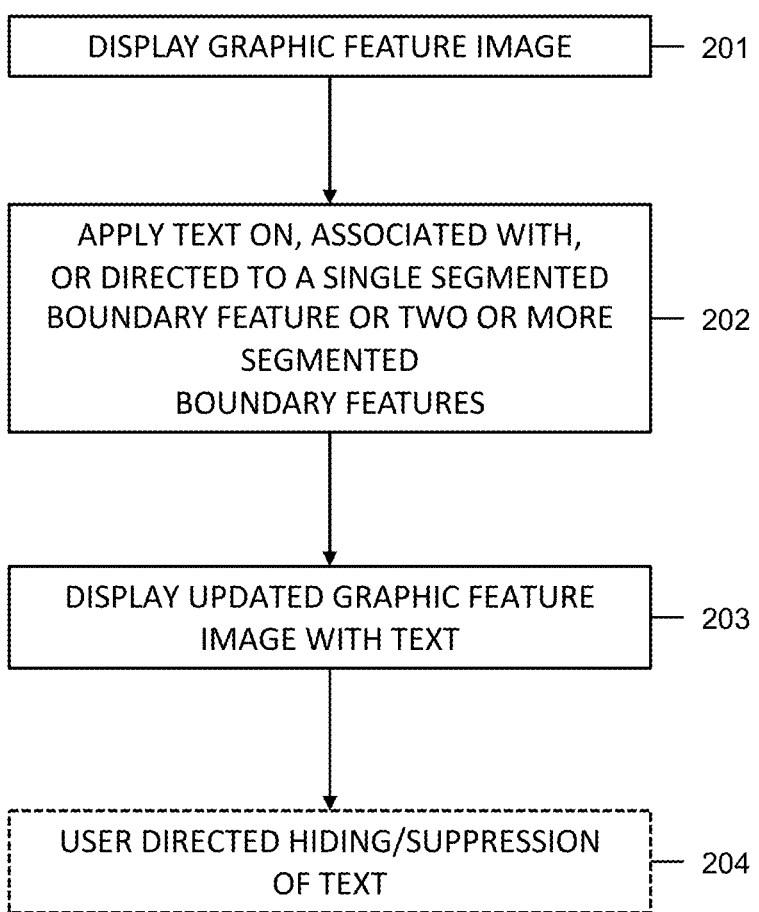
DISPLAY GRAPHIC FEATURE IMAGE — 201
APPLY TEXT ON, ASSOCIATED WITH, OR DIRECTED TO A SINGLE SEGMENTED BOUNDARY FEATURE OR TWO OR MORE SEGMENTED BOUNDARY FEATURES — 202
DISPLAY UPDATED GRAPHIC FEATURE IMAGE WITH TEXT — 203
USER DIRECTED HIDING/SUPPRESSION OF TEXT — 204
FIG. 2

300
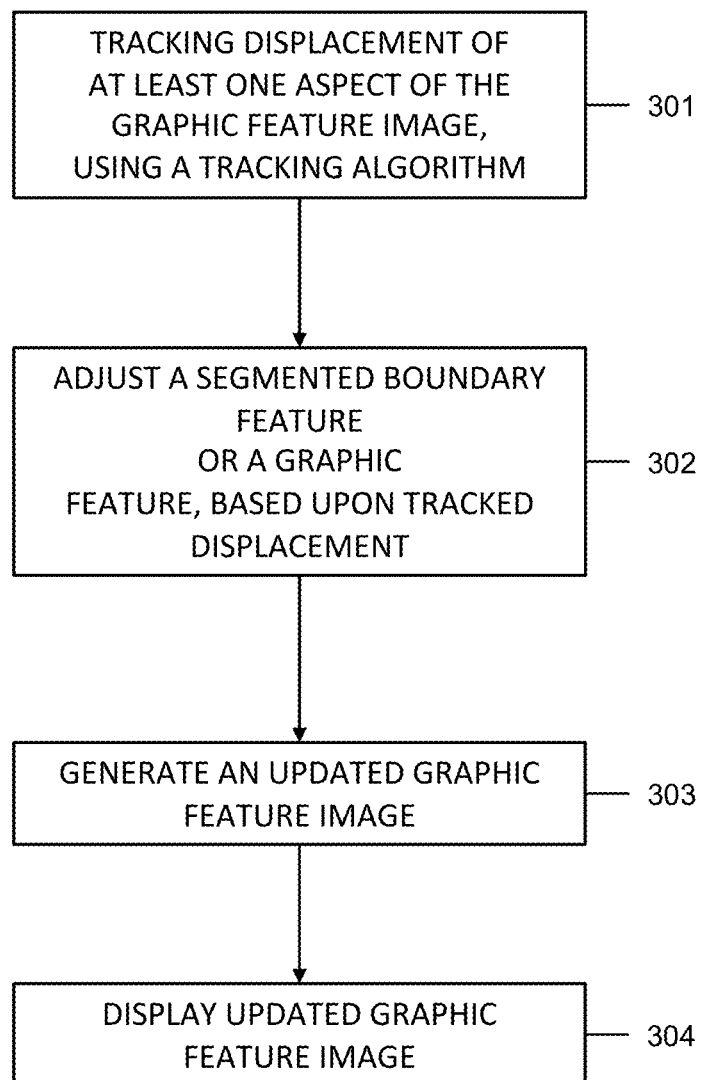
TRACKING DISPLACEMENT OF
AT LEAST ONE ASPECT OF THE
GRAPHIC FEATURE IMAGE,
USING A TRACKING ALGORITHM — 301
ADJUST A SEGMENTED BOUNDARY
FEATURE
OR A GRAPHIC
FEATURE, BASED UPON TRACKED
DISPLACEMENT — 302
GENERATE AN UPDATED GRAPHIC
FEATURE IMAGE — 303
DISPLAY UPDATED GRAPHIC
FEATURE IMAGE — 304
FIG. 3

400
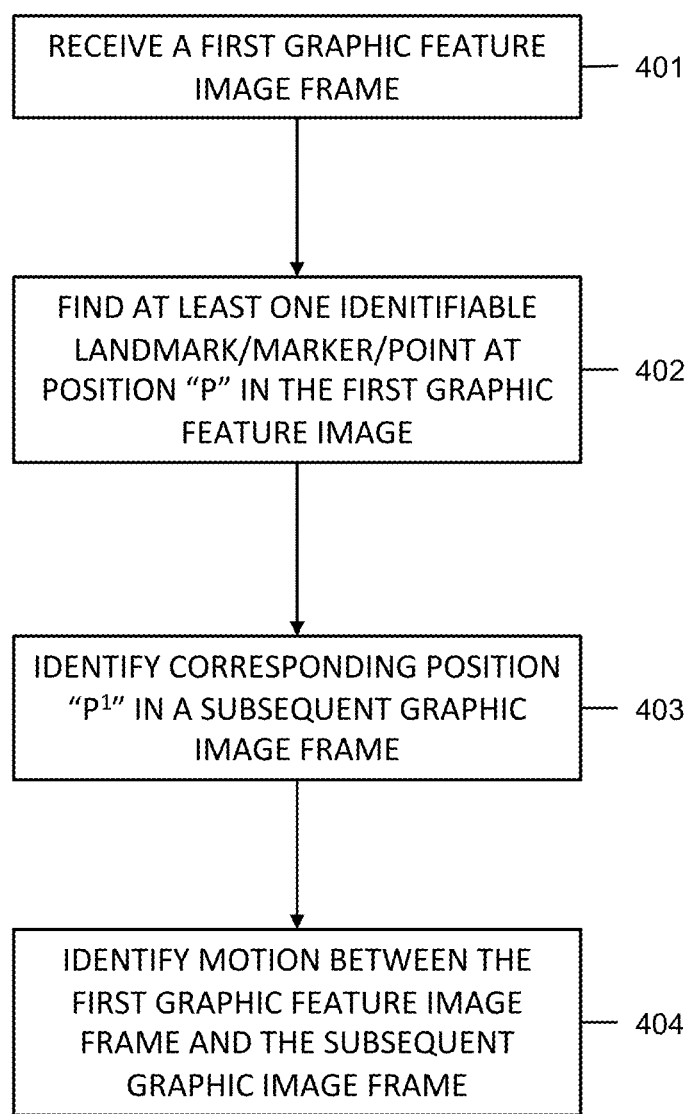
RECEIVE A FIRST GRAPHIC FEATURE
IMAGE FRAME —— 401
FIND AT LEAST ONE IDENITIFIABLE
LANDMARK/MARKER/POINT AT
POSITION "P" IN THE FIRST GRAPHIC
FEATURE IMAGE —— 402
IDENTIFY CORRESPONDING POSITION
"P¹" IN A SUBSEQUENT GRAPHIC
IMAGE FRAME —— 403
IDENTIFY MOTION BETWEEN THE
FIRST GRAPHIC FEATURE IMAGE
FRAME AND THE SUBSEQUENT
GRAPHIC IMAGE FRAME —— 404
FIG. 4

500

501

502

503

600

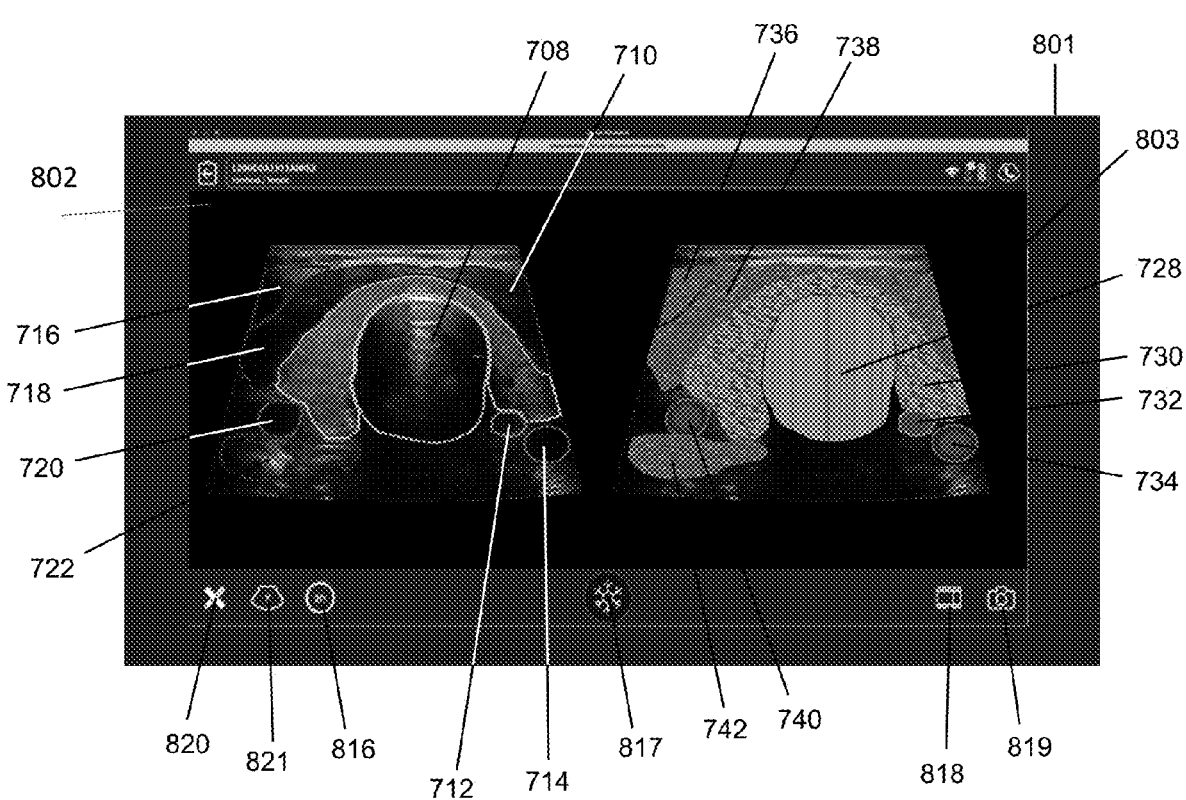
FIG. 8

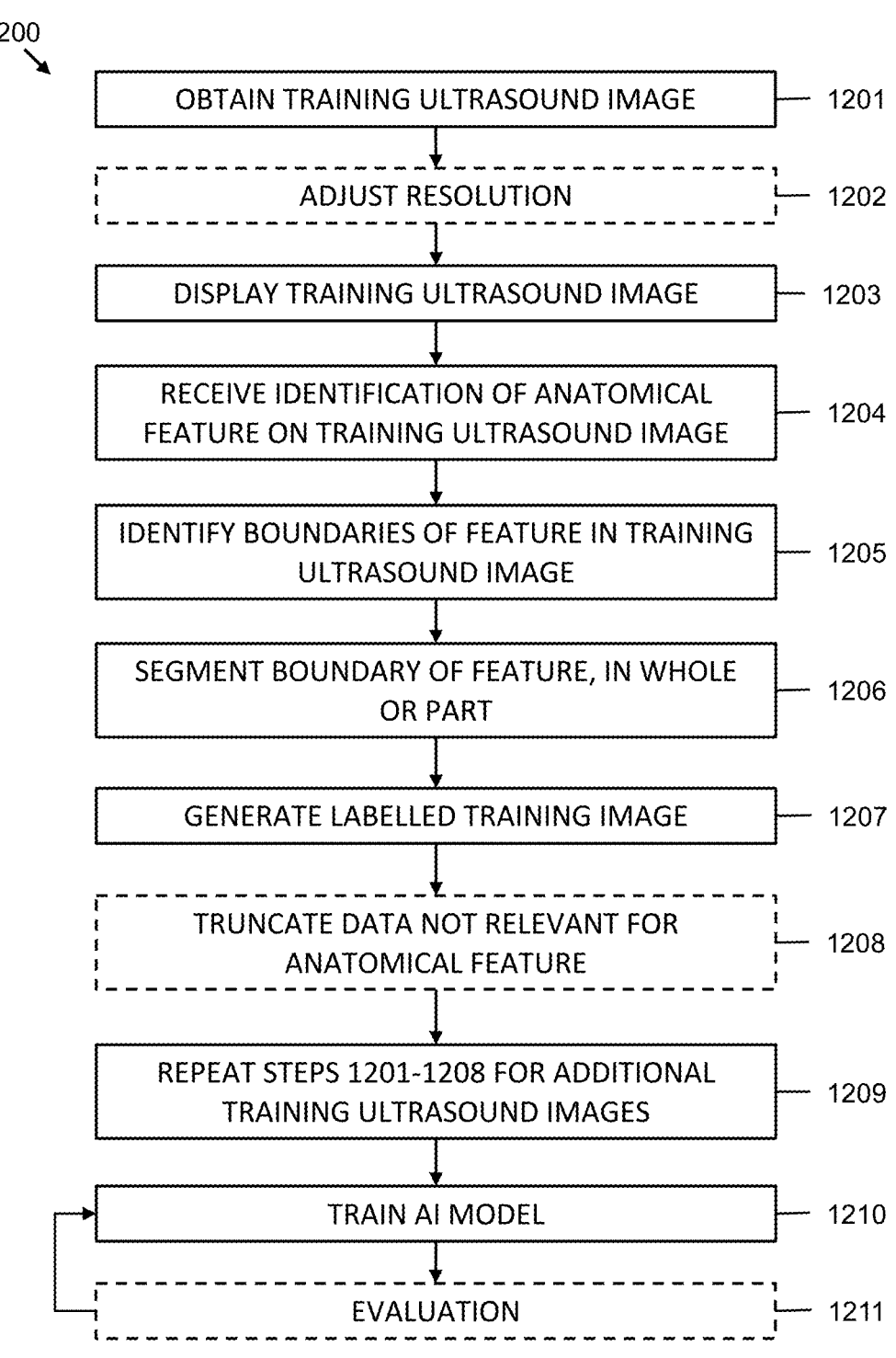

1200

| | |
|---|---|
| OBTAIN TRAINING ULTRASOUND IMAGE | 1201 |
| ADJUST RESOLUTION | 1202 |
| DISPLAY TRAINING ULTRASOUND IMAGE | 1203 |
| RECEIVE IDENTIFICATION OF ANATOMICAL FEATURE ON TRAINING ULTRASOUND IMAGE | 1204 |
| IDENTIFY BOUNDARIES OF FEATURE IN TRAINING ULTRASOUND IMAGE | 1205 |
| SEGMENT BOUNDARY OF FEATURE, IN WHOLE OR PART | 1206 |
| GENERATE LABELLED TRAINING IMAGE | 1207 |
| TRUNCATE DATA NOT RELEVANT FOR ANATOMICAL FEATURE | 1208 |
| REPEAT STEPS 1201-1208 FOR ADDITIONAL TRAINING ULTRASOUND IMAGES | 1209 |
| TRAIN AI MODEL | 1210 |
| EVALUATION | 1211 |

METHOD AND SYSTEM OF CREATING AND DISPLAYING A VISUALLY DISTINCT RENDERING OF AN ULTRASOUND IMAGE

FIELD

The present disclosure relates generally to ultrasound imaging, and in particular, to systems and methods for methods and systems of displaying a visually distinct rendering of an ultrasound image.

BACKGROUND

Ultrasound imaging systems are a powerful tool for performing real-time, non-invasive imaging procedures in a wide range of medical applications. An ultrasound machine includes a transducer which sends out ultrasound signals into tissue. Ultrasound waves are reflected back from the tissue and are received by the transducer. The reflected signals are processed to produce an ultrasound image of the target anatomy. An ultrasound machine typically has a user input device by which the operator of the ultrasound machine can control the machine to obtain images of tissue structures.

A challenging part of ultrasound technology is reading and understanding the generated images, particularly for less experienced users or training users. Ultrasound is historically one of the most operator-dependent medical imaging devices. An experienced, expert technologist can generate remarkably clear images from an ultrasound transducer, while a less experienced user might be unable to get images of appropriate quality even from the best equipment. Today, advances in artificial intelligence (AI), automation, specific presets which a user can select based upon scanning region of interest and live collaboration have all, to some extent, countered aspects of these traditional challenges; making the use of ultrasound scanners more accessible than ever. Despite improvements in quality of ultrasound images, there remains the challenge of understanding what is being viewed on ultrasound images, interpreting the content of the ultrasound images and identifying regions of interest. These challenges are due to a variety of factors.

First, the greyscale coloring of ultrasound images makes the images difficult to understand. Shading varies depending on how the sound waves bounce off the feature being scanned. For example, solid substances like bones will appear white, while fluid, like amniotic fluid and bladder contents, will appear dark or shades of grey. Second, sound waves do not reflect uniformly, and different kinds of visual artifacts (such as enhancement and attenuation) may occur in an ultrasound image depending on the settings of the ultrasound, the angle of the probe, or the density of the body's tissues.

These challenges in understanding the content and layout of generated ultrasound images are even more pronounced as ultrasound imaging is increasingly adopted by less experienced users. For example, these newer users may be in remote medical facilities, or in dermatology, facial aesthetics, and med spas or in triage settings or in veterinary practises. Additionally, in training ultrasound operators/ sonographers, medical schools, veterinary school, and other educational uses, it would be highly beneficial to provide visual methods to understand the content and layout of generated ultrasound images.

For at least these reasons, there is a need for improved systems and methods for generating a visually distinct rendering of an ultrasound image. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein. The above background information is provided to reveal information believed by the applicant to be of possible relevance to the present invention. No admission is necessarily intended, nor should be construed, that any of the preceding information constitutes prior art against the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Non-limiting examples of various embodiments of the present disclosure will next be described in relation to the drawings, in which:

FIG. 2 is flowchart diagram of an example method of the steps for additional text application onto i) a single segmented boundary feature or ii) at least two segmented boundary features, according to an embodiment of the present invention;

FIG. 3 is a flowchart diagram of an example method of tracking displacement of at least one aspect of the graphic feature image using a tracking algorithm, to direct adjustments to the graphic feature image within the segmented boundary features, according to an embodiment of the present invention;

FIG. 4 is a flowchart diagram of an example method of tracking a motion of one or more of an annotation and artifact associated with the segmented boundary feature, according to an embodiment of the present invention;

FIG. 8 is a schematic of a user interface display, showing on the left side am image comprising at least one segmented boundary feature and on the right side, the corresponding graphic feature image, with graphics applied onto the various segmented boundary features, for a thyroid application (neck scan), according to an embodiment of the present invention;

FIG. 12 is flowchart diagram of the steps for training the AI model, according to an embodiment of the present invention;

DETAILED DESCRIPTION

A. Glossary

Figure 1:
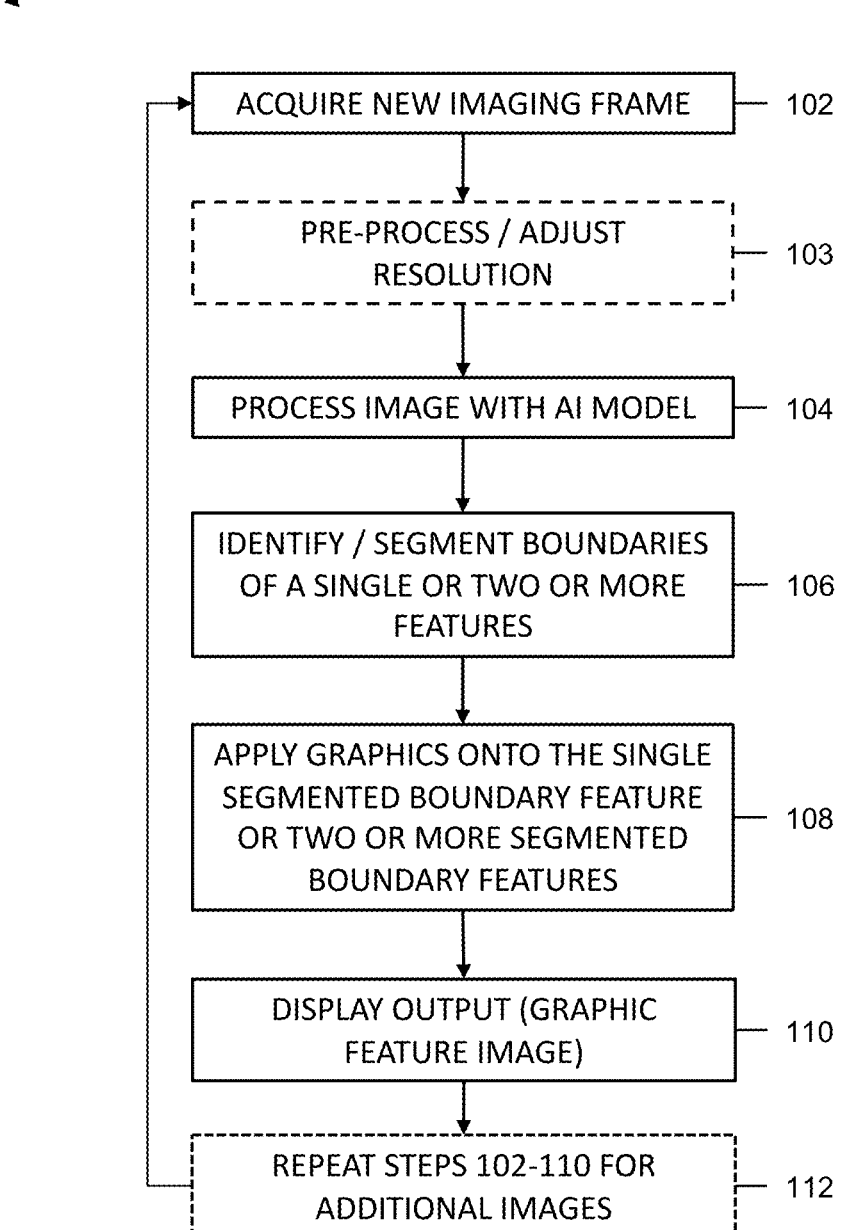
FIG. 1 is a flowchart diagram of an example method of image acquisition, creation of i) a single segmented boundary feature or ii) two or more segmented boundary features and graphic application, according to an embodiment of the present invention.

The term "AI model" means a mathematical or statistical model that may be generated through artificial intelligence techniques such as machine learning and/or deep learning. For example, these techniques may involve inputting labeled or classified data into a neural network (e.g., a deep neural network) algorithm for training, so as to generate a model that can make predictions or decisions on new data without being explicitly programmed to do so. Different software tools (e.g., TensorFlow™, PyTorch™, Keras™) may be used to perform machine learning processes.

The term "communications network" and "network" can include both a mobile network and data network without limiting the term's meaning, and includes the use of wireless (e.g. 2G, 3G, 4G, 5G, WiFi®, WiMAX®, Wireless USB (Universal Serial Bus), Zigbee®, Bluetooth® and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "feature" is intended to have broad meaning within the scope of the present invention, given that AI model identifies and segments boundaries of i) a single feature, in whole or part, creating one segmented boundary feature or ii) two or more features, in whole or part, creating two or more segmented boundary features, so that differentiating graphics may be applied to the segmented boundary feature(s). In other words, a single feature may be segmented by the AI model, such as for example a fetus or a single organ in isolation. Graphics may be applied only to this single feature, leaving the remainder of the image in B-mode (black and white). It is not required that every feature be identified and segmented and it is not required that every feature be applied with a graphic. The flexibility of how many features is segmented for graphic application may be built into various anatomy-specific programs and/or presets or may be selected and/or changed by a user, employing, for example user interface controls. For example, in FIG. 9, only the pancreas and liver may be segmented, for certain applications and training, leaving the remainder of the features in B-mode. This is about differentiation of a segmented feature(s), by the application of graphics in a way which has heretofore not been achieved and with a degree of flexibility as to use cases. Although some anatomical regions of the body lend themselves more readily to such segmentation and graphic application, the method and system of the invention offers advantages, particularly to novice and inexperienced users, across any region of the body. Without limiting the generality of the foregoing, feature may be selected from the group consisting of an organ, a portion of an organ, a boundary of an organ, a muscle, a boundary of a muscle, a blood vessel, a boundary of a blood vessel, a nerve, a boundary of a nerve, a fetus (in whole or part), a fat layer, epithelium, bodily fluid, a tumor, and a cyst.

The term "labeling" refers to an act of labeling either a piece of training data or non-training data. For example, a user may mark a feature on an ultrasound image and identify the anatomy to which the feature corresponds. The result is a labeled piece of data, such as a labeled ultrasound image. Alternatively, and by way of example, an AI model may automatically and without user intervention label one or more segmented features, within an ultrasound image.

The term "module" can refer to any component in this invention and to any or all of the features of the invention without limitation. A module may be a software, firmware or hardware module (or part thereof), and may be located or operated within, for example, in the ultrasound scanner, a display device or a server.

The term "multi-purpose electronic device" or "display device" or "computing "device" is intended to have broad meaning and includes devices with a processor communicatively operable with a screen interface, for example, such as, laptop computer, a tablet computer, a desktop computer, a smart phone, a smart watch, spectacles with a built-in display, a television, a bespoke display or any other display device that is capable of being communicably connected to an ultrasound scanner. Such a device may be communicatively operable with an ultrasound scanner and/or a cloud-based server (for example via one or more communications networks).

The term "operator" (or "user") may (without limitation) refer to the person that is operating an ultrasound scanner (for example, a clinician, medical personnel, aesthetics professional, dentist, a sonographer, student, vet, sonographer/ultrasonographer and/or ultrasound technician). This list is non-exhaustive.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "rendering engine" as used herein refers to software that draws, manipulates, alters or re-arranges one or more of graphics, text and images on a screen. More specifically, a rendering engine may reproduce a graphic feature image in which one or more graphics are applied upon a single segmented boundary feature or two or more segmented boundary features, in which a graphic feature image is an is "output". As described herein in detail, a rendering engine can create realistic graphics, lighting, shadows, atmosphere, color, texture and optical effects such as light refraction or blur seen on moving objects.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for generating and displaying a visually distinct rendering of an ultrasound image. In various embodiments, the system may include an ultrasound scanner and a multi-purpose electronic device/display device; and/or an ultrasound scanner, multi-purpose electronic device/display device and a server. The system may include one or more applications operating on a multi-purpose electronic device/display device to which the ultrasound scanner is communicatively connected.

The term "ultrasound image frame" (or "image frame" or "ultrasound frame") refers to a frame of either pre-scan data or post-scan conversion data that is suitable for rendering an ultrasound image on a screen or other display device.

The term "ultrasound transducer" (or "probe" or "ultrasound probe" or "transducer" or "ultrasound scanner" or "scanner") refers to a wide variety of transducer types including but not limited to linear transducer, curved transducers, curvilinear transducers, convex transducers, micro-convex transducers, and endocavity probes. In operation, an ultrasound scanner is often communicatively connected to a multi-purpose electronic device/display device to direct operations of the ultrasound scanner, optionally through one or more applications on the multi-purpose electronic device/display device (for example, via the Clarius™ App).

B. Exemplary Embodiments

This description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

At a high level, the embodiments herein generally allow for the generation of a unique, visual ultrasound image product wherein segmented features, within an ultrasound image, are layered with distinguishing graphics to aid in the identification and delineation of one or more anatomical features. More specifically, an ultrasound image is processed against an AI model to identify and segment boundaries of i) a single feature in whole or part, on the ultrasound image, thereby creating one single segmented boundary feature or ii) two or more features, in whole or part, on the ultrasound image, thereby creating two or more segmented boundary features and subsequently a graphic is applied onto segmented boundary feature(s), thereby forming a graphic feature image. For greater clarity, with the embodiment of the invention, a graphic is anchored or layered onto one or more segmented boundary features, thereby forming a graphic feature image from which is generated an output image, on a screen, comprising the graphic feature image. This graphic feature image, generated into an output image, provides a visual tool for novice and experienced ultrasound users alike to quickly and easily ascertain and classify the parts of the anatomy being scanned.

In a first broad aspect of the present disclosure, there are provided ultrasound systems and ultrasound-based methods for generating a graphic feature image which may be displayed as an output image on a screen. This output image, comprising at least one graphic feature image, as defined further herein, is prepared for and directed to a wide variety of applications including, but not limited to training ultrasound operators/sonographers, in medical schools, in veterinary schools, for ultrasound image assessment in remote medical facilities, by those in medical fields which would not traditionally have employed ultrasound, for example, in dermatology, facial aesthetics, and med spas and by any ultrasound user seeking an easy way to ascertain and classify the parts of the anatomy being scanned.

In another aspect of the present disclosure, there is provided a method for creating and displaying a visually distinct rendering of an ultrasound image, acquired from an ultrasound scanner, the method comprising displaying, on a screen that is communicatively connected to the ultrasound scanner, an ultrasound image feed comprising ultrasound image frames; deploying an AI model to execute on a computing device communicably connected to the ultrasound scanner, wherein the AI model is trained so that when the AI model is deployed, the computing device identifies and segments boundaries of a single feature or two or more features, in whole or part, acquiring, at the computing device, a new ultrasound image during ultrasound scanning, processing, using the AI model, the new ultrasound image to identify and segment boundaries of a single feature or two or more features, in whole or part, on the new ultrasound image, thereby creating respectively, either a single segmented boundary feature or two or more segmented boundary features, applying a graphic onto the segmented boundary feature(s), thereby forming a graphic feature image and generating an output image, on the screen, comprising the graphic feature image.

In another aspect of the present disclosure, there is provided a system for generating and displaying a visually distinct rendering of an ultrasound image, comprising an ultrasound scanner configured to acquire a new ultrasound image frame, a computing device communicably connected to the ultrasound scanner and configured to process the new ultrasound image frame against an artificial intelligence model to identify and segment boundaries of i) at least one feature in whole or part, on the ultrasound image, thereby creating one segmented boundary feature or ii) two or more features, in whole or part, on the ultrasound image, thereby creating two or more segmented boundary features and subsequently a graphic is applied onto the segmented boundary feature(s), thereby forming a graphic feature image, to generate an output image comprising the graphic feature image and wherein the system also comprises a display device configured to display the output image comprising the graphic feature image.

In another aspect of the present disclosure, there is provided a computer-readable media storing computer-readable instructions, which, when executed by a processor cause the processor to process a new ultrasound image frame against an artificial intelligence model to identify and segment boundaries of i) a single feature in whole or part, on the ultrasound image, thereby creating one segmented boundary feature or ii) two or more features, in whole or part, on the ultrasound image, thereby creating two or more segmented boundary features and subsequently a graphic is applied onto segmented boundary feature(s), thereby forming a graphic feature image and generate and display an output image comprising the graphic feature image on a display screen.

In another aspect of the present disclosure, there is provided a touchscreen device which is capable of communicating with an ultrasound scanner, the touchscreen device includes: a processor; and a memory storing instructions for execution by the processor, a interface user trigger for initiating the steps of: i) automatic identification and segmentation, by an artificial intelligence model, of boundaries of i) a single one; or ii) two or more features, in whole or part, on an ultrasound image frame, thereby creating i) a single segmented boundary feature; or ii) two or more segmented boundary features; ii) automatic application of a graphic onto the segmented boundary feature(s), thereby forming a graphic feature image; and iii) display of an output image comprising the graphic feature image on a display screen.

In another aspect of the present disclosure, there is provided a workflow tool for generating and displaying a visually distinct rendering of an ultrasound image, in real-time and while scanning, without a requirement for any additional user inputs. Along with these workflows, the present invention comprises the underlying graphical user interface organized to deploy the method of the invention, including an optional user selection of one or more ultrasound image frames for processing through the method of the invention. This workflow tool may be implemented through an ultrasound scanner, or through a multi-use device communicatively associated with an ultrasound scanner or through an application operated though a cloud-based server communicatively associated with one or both of an ultrasound scanner and a multi-use device. A graphical user interface organized to deploy the method of the invention may be viewable on a screen, for example a touchscreen, on a multi-use device communicatively associated with an ultrasound scanner.

In present invention, an artificial intelligence (AI) model is trained on a plurality of ultrasound images of anatomy/anatomical features, for the purpose of feature/boundary segmentation as described further below. These images enable the AI model to be trained so that when the AI model is deployed, a computing device communicably connected to an ultrasound scanner, identifies and segments boundaries of features, in whole or part, thereby creating at i) least one segmented boundary feature; or ii) two or more segmented boundary features, upon which at least one graphic may be applied. As such, the present invention further provides, in another aspect, such a trained and deployable AI model.

The present invention provides, in another aspect, one or more output images comprising one or more graphic feature images such graphic feature images formed by the method of the present invention. A collection of one or more output images may comprise a visual image product which may be saved, collected with other output images, and/or formed into an enhanced media product such as, for example, a video or other media product for training and reference purposes. It is to be understood that media product as used herein comprises images, and/or videos and/or cineloops and which is rendered using a media rendering program/system, using ultrasound images generated (and optionally labelled, annotated and captioned) using the AI model and graphic application module of the present invention. The media product may be a video written to a physical media (such as a Compact Disc-Recordable (CD-r) or a Digital Video Disc (DVD) or made available online through cloud-based storage, through electronic communication or other transfer and data sharing means. Such media product may comprise, in addition to the graphic overlays on the two or more boundary features, annotations and/or text overlays. In some embodiments, the media product may comprise a plurality of cineloops.

In another broad aspect of the present disclosure, there is provided a server including at least one processor and at least one memory storing instructions for execution by the at least one processor, wherein when executed, the instructions cause the at least one processor to process an ultrasound image frame against an artificial intelligence model to identify and segment boundaries of i) at least one feature in whole or part, on the ultrasound image, thereby creating one segmented boundary feature or ii) two or more features, in whole or part, on the ultrasound image, thereby creating two or more segmented boundary features, to apply a graphic onto the at least one or two or more segmented boundary features, thereby forming a graphic feature image and to generate and display an output image comprising the graphic feature image on a display screen.

In another broad aspect of the present disclosure, there is provided a computing device comprising at least one processor and at least one memory storing instructions for execution by the at least one processor, wherein when executed, the instructions cause the at least one processor to, using a trained AI model, identify and segment boundaries of i) a single feature; or ii) two or more features, in whole or part, on the new ultrasound image, thereby creating i) a single segmented boundary feature or ii) two or more segmented boundary features, apply a graphic onto the segmented boundary feature(s), thereby forming a graphic feature image; and generate an output image, on the screen, comprising the graphic feature image.

The present invention provides, in another aspect, a method of training an artificial intelligence (AI) model which is deployed to execute on a computing device communicably connected to the ultrasound scanner, wherein the AI model is trained so that when the AI model is deployed, the computing device identifies and segments boundaries of a feature or features, in whole or part on an ultrasound image, thereby creating i) a single segmented boundary feature; or ii) two or more segmented boundary features so that, thereafter, a graphic may be applied onto the single segmented boundary feature or two or more segmented boundary features, thereby forming a graphic feature image.

There are variety methods which may be employed in AI based segmentation of ultrasound images, and the present invention is not intended to be limited to any one of these methods. Image segmentation refers to the detection of boundaries of features and structures, such as, but not limited to organs, vessels, different types of tissue in ultrasound images. In an embodiment of the present invention, a method deploys a trained AI model to perform intelligent automated recognition of segmentation tasks and intelligent automated selection and application of segmentation algorithms. This allows the AI model to be applied to intelligently perform various different segmentation tasks, including segmentation of different anatomical structures and features. The AI model can intelligently select one or a combination of segmentation algorithms from a plurality of segmentation algorithms to perform appropriate segmentation for various features and anatomical object. For example, the algorithms may be a threshold-based segmentation algorithm, an edge-based segmentation algorithm, a region-based segmentation algorithm, a clustering-based segmentation algorithm, or the like, or a combination thereof.

In some embodiments of the invention, segmentation algorithms may be stored in a segmentation algorithm database which may comprise a plurality of deep learning-based ultrasound image segmentation methods, each of which including a respective trained deep neural network architecture for performing ultrasound image segmentation. For example, the segmentation algorithms can include the deep learning based segmentation algorithms described below, including segmentation using a deep neural network (DNN) that integrates shape priors through joint training, non-rigid shape segmentation method using deep reinforcement learning, segmentation using deep learning based partial inference modeling under domain shift, segmentation using a deep-image-to-image network and multi-scale probability maps, and active shape model based segmentation using a recurrent neural network (RNN). The segmentation algorithm database may include other deep learning-based segmentation algorithms as well, such as marginal space deep learning (MSDL) and marginal space deep regression (MSDR) segmentation methods. It is also possible that a segmentation algorithm database may also store various other non-deep learning-based segmentation algorithms, including but not limited to machine-learning based segmentation methods (e.g., marginal space learning (MSL) based segmentation), graph cuts segmentation methods, region-growing based segmentation methods, and atlas-based segmentation methods.

A segmentation algorithm database may store multiple versions of each segmentation algorithm corresponding to different target anatomical features and structures. For deep learning-based segmentation algorithms, each version corresponding to a specific target anatomical structure may include a respective trained deep network architecture with parameters (weights) learned for segmentation of that target anatomical structure. For a particular anatomical structure, a segmentation algorithm database can also store multiple versions corresponding to different imaging domains and/or image quality levels. For example, different deep learning architectures can be trained and stored using images with different signal-to-noise ratios. Accordingly, when a master segmentation artificial agent selects one or more segmentation algorithms from the those stored in a segmentation algorithm database, the master segmentation artificial agent may select not only the type of segmentation algorithm to apply, but the specific versions of segmentation algorithms that are best for performing the current segmentation task.

In some embodiments, the ultrasound frames of a new ultrasound image, imaged in ultrasound imaging data may be processed against an AI model on a per pixel basis, and thus the segmentation of boundaries of features, in whole or part, on the new ultrasound image, thereby creating one segmented boundary feature or two or more segmented boundary features, imaged in new ultrasound imaging data, may be generated on a per pixel basis. When deployed, an output of the AI model for a first pixel of the new ultrasound imaging data may be used to corroborate the output of the AI model for a second pixel of the new ultrasound imaging data adjacent or within the proximity to the first pixel.

Alternatively, the ultrasound frames of new ultrasound images, imaged in ultrasound imaging data may be processed against an AI model on a line/sample basis, and the and thus the segmentation of boundaries of the feature or features, in whole or part, on the new ultrasound image, thereby creating at least one or two or more segmented boundary features, imaged in new ultrasound imaging data, may be generated on a line/sample basis.

Within the scope of the present invention, an AI model may be deployed to identify and create i) a single segmented boundary feature; or ii) two or more segmented boundary features, imaged in new ultrasound imaging data, iii) in some cases three or more and iv) in other cases greater than four segmented boundary features. The number of features to preferably be segmented will depend, for example, on the region of anatomy being imaged (for example, the size and number of features contained therein, complexity of ROI within the region of anatomy) and also the purpose of the graphic feature image. For example, in an abdominal scan, as described further below, it may be advantageous, in some views and for some purposes, to identify and segment three, four or five differing features, to apply a differentiating graphic onto the each of segmented boundary features, thereby forming a graphic feature image, for ease in understanding the content of the entire ultrasound image. Conversely, in some ultrasound images, one feature is preeminent, and segmentation of that single feature is desired, for example, an ultrasound image of a fetus, in particular an advanced stage fetus (see for example, FIG. 16). For greater clarity, it is to be understood that not every feature within a region of interest (ROI) being scanned and shown in an ultrasound image will need to be segmented and overlayed with a graphic. Further, not every feature within a region of interest (ROI) being scanned and shown in an ultrasound image, although segmented, will need to be overlayed with a graphic. The benefit of the method and system of the invention is the formation of a graphic feature image which is of assistance in quickly and easily understanding salient, composite pieces of an ultrasound image, and not necessarily every single anatomical feature within a region of interest (ROI) being scanned and within the ultrasound image.

Furthermore, how many anatomical features are segmented and/or applied with a graphic may be dependent on use cases and specific requirements thereof. In an educational context, for example, directed to medical students, veterinary students, nursing students, sonography students and the like, it may be beneficial, in an ultrasound image, to segment a greater number of features and also apply graphics to a greater number of segmented boundary feature(s), thereby forming one or more graphic feature image(s) for generation of one or more output image(s) which form a complete textbook-like appearance on a screen, optionally including text or other annotations on the graphic feature image or within the segmented boundaries. This type of graphic differentiation of features, similar to illustrations shown in textbooks, such as Gray's Anatomy: The Anatomical Basis of Clinical Practice, but heretofore not created as part of actual ultrasound images, provides a compelling, highly visual and adaptable ultrasound tool. Conversely, a user such as an experienced internist may only wish to create an output image/graphic feature image comprising segmented boundaries around each of the liver, kidney, spleen and gallbladder, but with graphics applied only to the segmented boundaries of the pancreas and liver. Such is the versatility and adaptability enabled by the embodiments of the present invention.

Figure 6:
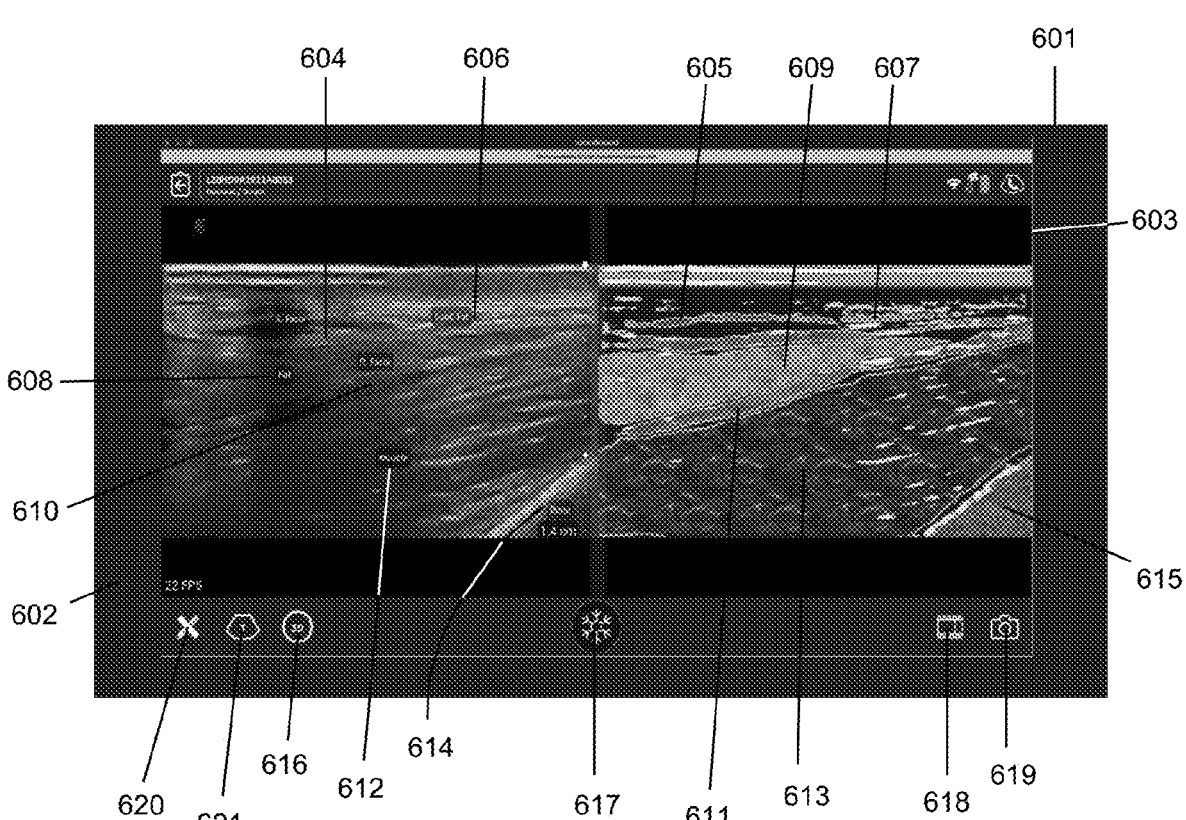
FIG. 6 is a schematic of a user interface display, showing on the left side am image comprising two or more segmented boundary features and on the right side, the corresponding graphic feature image, with graphics applied onto the various segmented boundary features, for an aesthetics application (facial scan), according to embodiment of the present invention.
Figure 9:
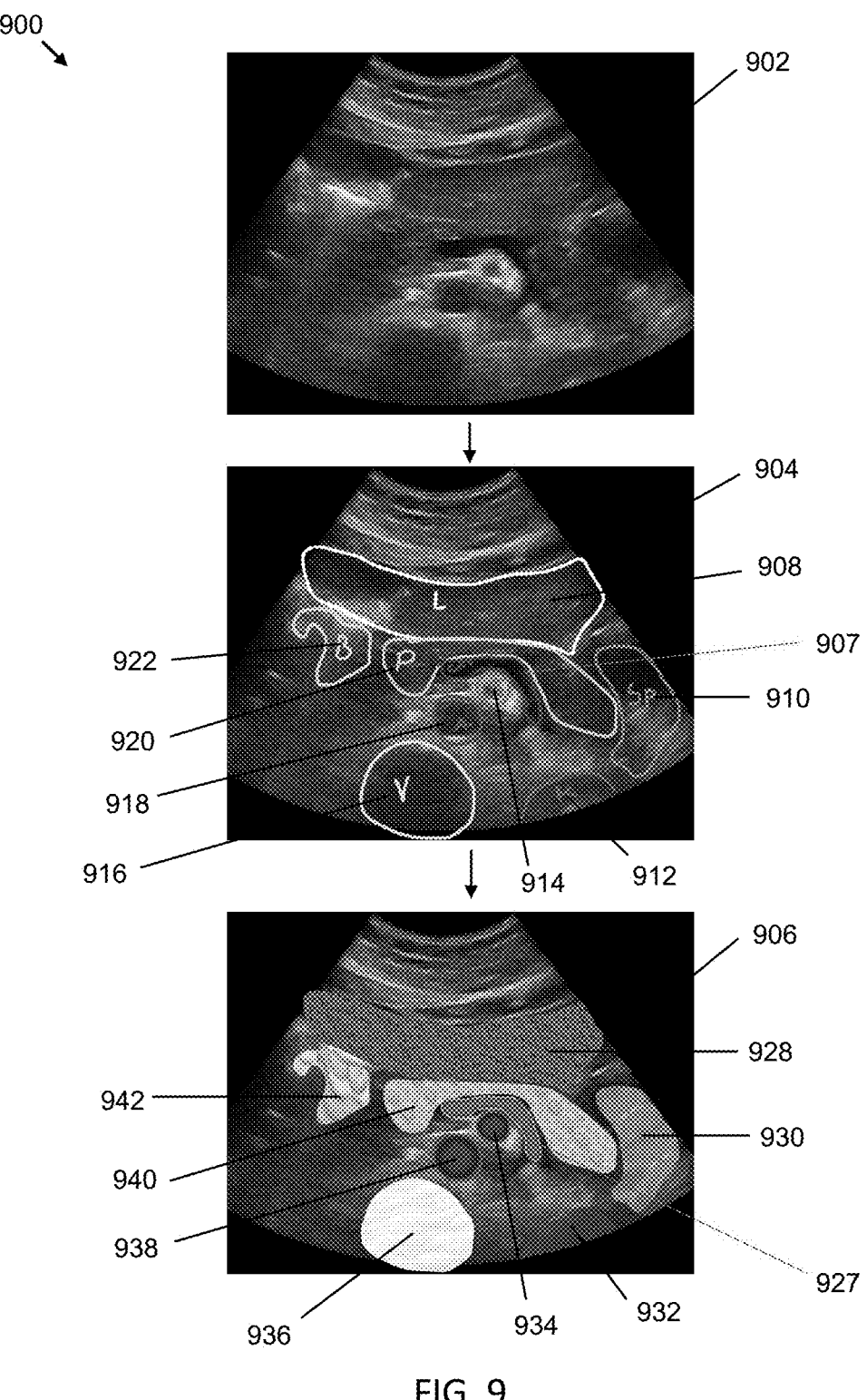
FIG. 9 is a schematic of the progression of images, from a B-mode ultrasound image, to a subsequently created segmented image to a graphic feature image, for an abdominal scan, according to an embodiment of the present invention.
Figure 10:
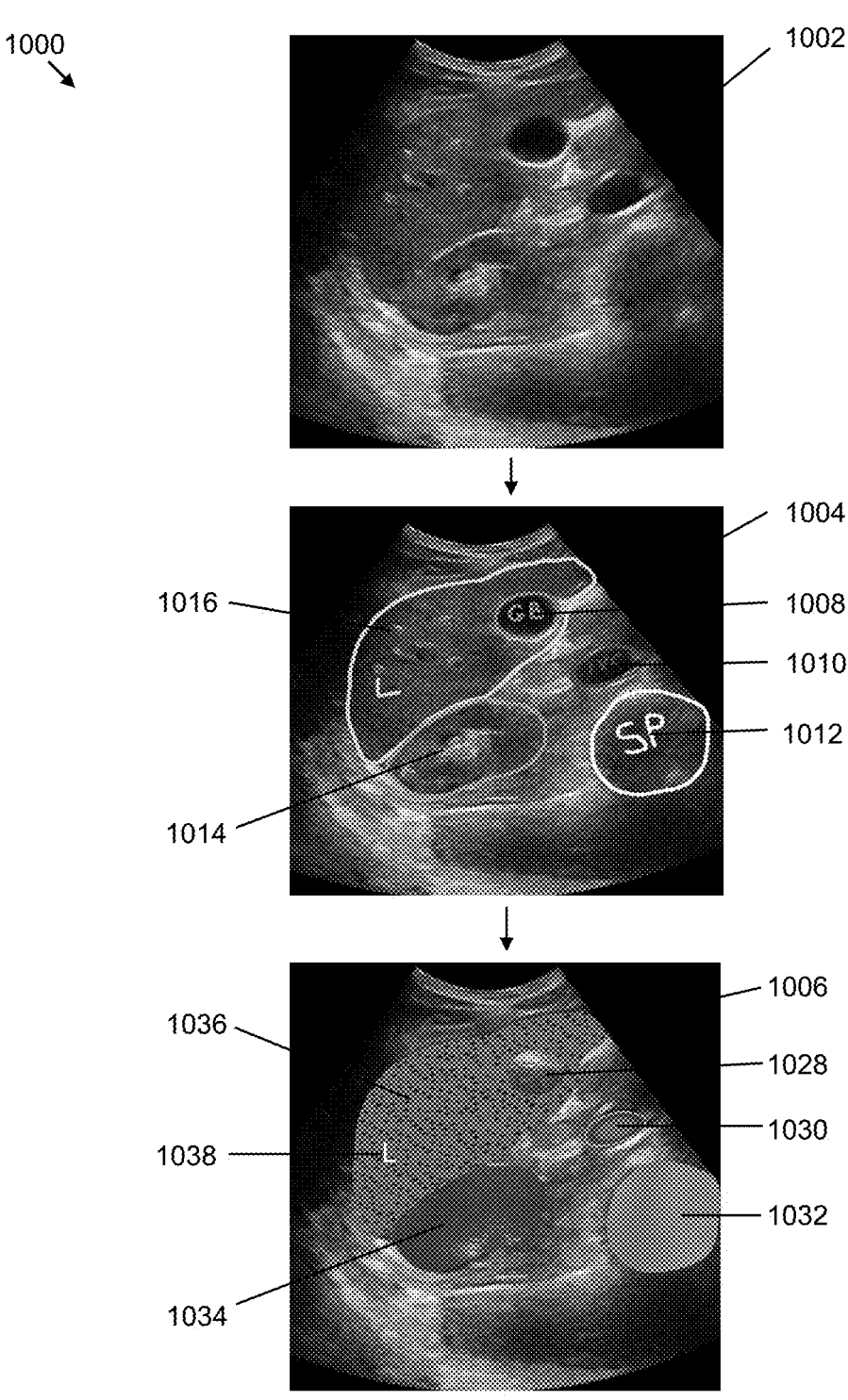
FIG. 10 is an additional schematic of the progression of images, from a B-mode ultrasound image, to a subsequently created segmented image to a graphic feature image, for an abdominal scan, according to an embodiment of the present invention.
Figures 17A, 17B, 17C:
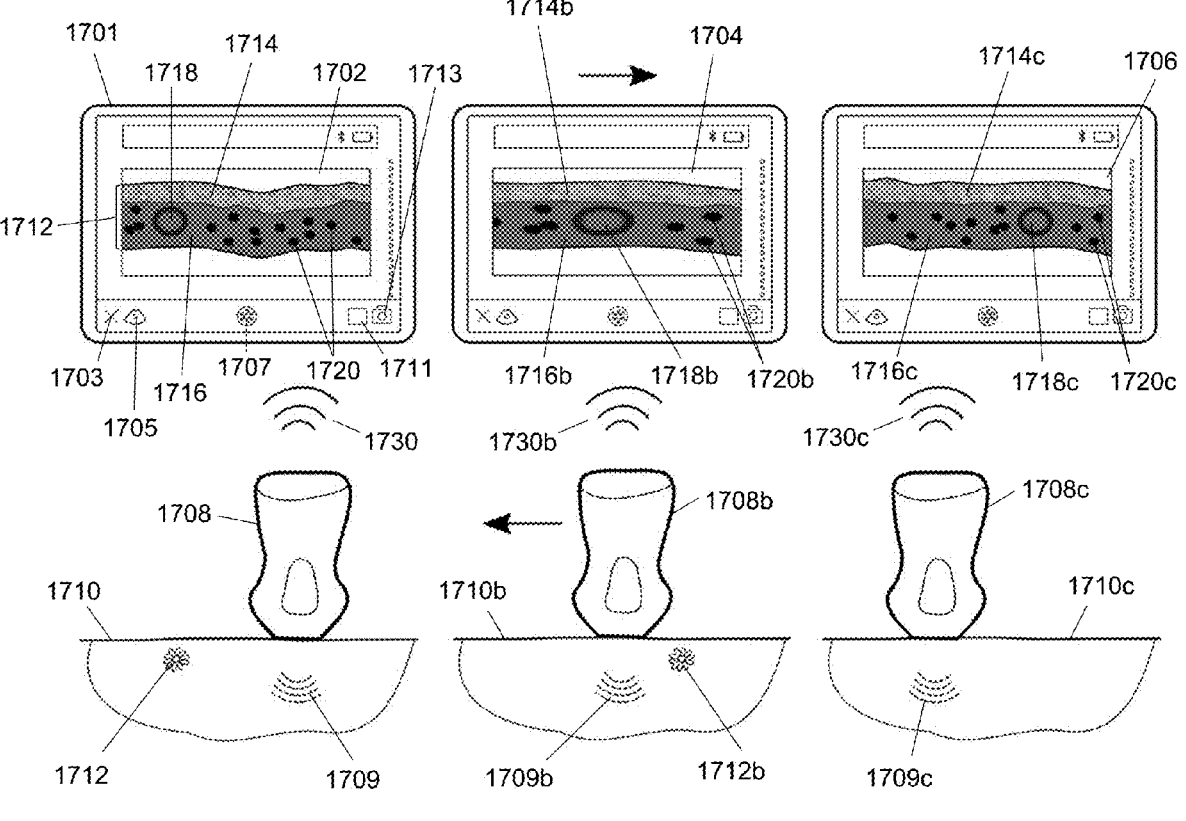
FIG. 17A is a schematic, along with FIGS. 17B and 17C, of a depiction of motion, both as a graphic feature image is displayed on a screen and as an ultrasound scanner in positioned over a patient, with FIG. 17A being a stationary first position.
FIG. 17B is a schematic along with FIGS. 17A and 17C, of a depiction of motion, both as a graphic feature image is displayed on a screen and as an ultrasound scanner moves, with FIG. 17B showing a scanner in motion and a respective view of a moving graphic feature image on a screen.
FIG. 17C is a schematic along with FIGS. 17A and 17B, of a depiction of motion as an ultrasound scanner, with FIG. 17C being an ultrasound scanner in a stationary second position, consequent to the motion shown in FIG. 17B.

With the scope of the embodiments of the present invention, a graphic is applied onto the i) a single segmented boundary feature; or ii) two or more, segmented boundary features, thereby forming a graphic feature image. A graphic is, without limitation, any visual representation such as, for example, color, hue, contrast, shading, brightness, patterns, animation, line art, symbols, geometric designs, photorealistic designs, artistic designs, bitmap graphics, and vector graphics. In some embodiments, textures as applied which would be typical of familiar illustrations for that specific anatomy, comprising the segmented feature. For example, as shown in FIG. 6, segmented superficial adipose tissue (fat) in the facial area comprising at fat cells within fat lobules, which are within palisading columnar fat pearls, are texturized with a mottled, off-yellow color. In FIGS. 9 and 10, segmented liver tissue is texturized with a spotted brown design. In some embodiments, these graphics and textures may be photorealistic to the segmented feature they are representing and in other embodiments, they may not. In some embodiments, these graphics and textures may be hyper-colored and contrasted to appear almost cartoon-like. In some embodiments, these graphics and textures may be applied in a way which optimizes the optional step of tracking displacement of at least one aspect of the graphic feature image using a tracking algorithm, to direct adjustments to the graphic feature image within the segmented boundary features. In this way, and as desired, some graphics and textures may be purposely selected to show movement in a more visually obvious and distinct way. For example, as shown in FIGS. 17A-17C below, the graphic comprising one large blue circle and a plurality of smaller black circles readily shows motion by stretching or elongation of the circles to form ovals. Graphics that can, for example, be stretched, size-changed, tone or brightness altered, muted, morphed or color changed in some way to depict motion may also be employed for this purpose.

Graphics/texture may be applied using procedural texture generation and texture generation such as, for example, bitmap graphics or vector graphics. A bitmap (also called "raster") graphic is created from rows of different colored pixels that together form an image. In their simplest form, bitmaps have only two colors, with each pixel being either black or white. With increasing complexity, an image can include more colors (photograph-quality images may have millions). Examples of bitmap graphic formats include GIF, JPEG, PNG, TIFF, XBM, BMP, and PCX as well as bitmap (i.e., screen) fonts. As such, the output image of the present invention, showing the graphic feature image on a screen, is also a bitmap. Bitmap generation may be through paint programs such as Adobe Photoshop®.

Vector (also known as "object-oriented") graphics are constructed using mathematical formulas describing shapes, colors, and placement. Rather than a grid of pixels, a vector graphic consists of shapes, curves, lines, and text which together form a texture, within the scope of the invention. While a bitmap image contains information about the color of each pixel, a vector graphic contains instructions about where to place each of the components. Further, it is possible to embed a bitmap graphic within a vector graphic, forming a graphic/texture which is a vector-bitmap hybrid.

Alternatively, and similarly within the embodiments of the present invention, a graphic may be applied onto a segmented boundary feature, thereby forming a graphic feature image using parameterized texture model comprising the generation of one or more underlying noise fields, using, for example, simplex noise, cellular noise, Perlin noise or fractal noise, which may then be processed using a plurality of parameterized functions controlled by a set of parameters. Alternatively, or additionally, the generation of a texture using the parameterized texture model may comprise computing fractal procedural textures based on a set of parameters, including the generation of detail over a plurality of different length scales. Alternatively, or additionally, the generation of a texture using the parameterized texture model may comprise using a compositional pattern-producing network.

One important aspect in creating a graphic feature image, which is a rendered image, is the creation of attributes for the surfaces and optionally the interiors of objects. Optical attributes can include color; transparency; reflective and refractive properties (such as diffuse and specular reflective coefficients; and geometric properties (such as surface normal and displacement vectors). Attribute data sets can be generated in a number of ways. A technician can manually create data sets such as texture maps by drawing an image of the desired data set, which is impractical within the scope of the invention. Other software tools can be used to manually define other types of attribute data sets, such as surface normal or displacement vectors. Additionally, data sets can be generated procedurally. Typically, procedural data sets are created by applying one or more algorithms to one or more input data sets. In some applications, only the algorithms and input data sets for a procedural data set are defined in advance of rendering. During rendering, the procedural data is produced as needed for only the portions of objects being rendered. Procedural data sets can be used to approximate the look and attributes of a variety of different anatomical features.

One type of input data is noise. Noise is a set of random, pseudorandom, or other type of data without any discernable pattern. Data having a discernable pattern may also have a noise component, which is the portion of the data without a discernable pattern. Noise is used by procedural data sets to introduce natural variations in the attributes of an object and to ensure that no unnatural repeating patterns occur. Common types of noise used by procedural data sets include Perlin noise and fractal noise. These types of noise create a noise set by combining two or more octaves of random or pseudo randomly generated data. An octave is a set of data having a frequency spectrum contained between two frequencies that have a two to one ratio. By combining octaves of data, Perlin noise attempts to bandlimit the resulting noise to a desired frequency spectrum. The Fractal Noise effect uses Perlin noise to create grayscale noise that may be employed to apply graphics and textures to the segmented boundary features. Fractal noise combines several "layers" of noise with increasing scales and often by also decreasing intensity. Within fractal noise algorithms, there are layers, called Octaves, a scale called Frequency, and an intensity, known as Gain. Thus, increasing the scale results in an incrementally smaller noise (hence "fractal"): the noise will be the same but just smaller. Fractal noise is employed widely in the field of computer graphics, and similarly may be used herein to generate and apply graphics within the scope of one aspect of the invention.

As and if required, when applying graphics and textures to the segmented boundary features, segmented boundary edges may be blended to minimize the edges in applying graphics/texture (for example to minimize background color and shading). This may be achieved in a variety of way including by inflating AI segmented boundaries. Temporal median may be used on one or more frames to assist in reducing and/or avoiding blinking on a graphic feature image. As there is grayscale (B-mode) ultrasound around the region of the one or more segmented features, in an embodiment of the invention, the distance between two or more segmented features may be calculated thereby to stretch or blend regions to create a more cohesive look to the graphic feature image and to minimize gaps between the segmented features. The calculation may use the number of pixels between features or apply a more complex algorithm such as determining the feature type (organ, muscle, adipose tissue), and then making an appropriate determination on how much the segmented feature can blend over the grayscale data into the adjacent feature.

In addition, interpolation processing may be applied to fill missing holes (i.e., pixels) in the resulting graphic feature image. For example, a bicubic interpolation may be applied which leverages neighboring elements of a two-dimensional block. Filtering (for example median filtering) may also be used to fill gaps between two or more segmented features. In order to improve the accuracy of distance/tracking estimation, image data may optionally be processed with a digital filter. One suitable tool is a median filter, which is a non-linear digital filter used in image and signal processing to remove impulse noise and smooth signals. The process of median filtering is to obtain the signal values in the form of a variational series built in ascending or descending order. Signal values are taken in the vicinity of a selected point (filter window). To determine the distance of a moving artifact or feature the median filter selects a cloud of points from the input images using nearby data. Thus, if a filtered selection of array elements is D={d1, d2, . . . , dn}, so that the number of selection elements coincides with the size of the filter window, then the application of median filtering, which selects the central values of the ordered selection, can be written as:

$$x* = med(d1, d2, \ldots, dn)$$

In the application of graphics/texture, regardless of using procedural texture generation, parameter texture generation or other means, it is to be understood that there are a variety of means for linking and overlaying a particular graphic or texture to a segmented feature. In one aspect of the invention, a graphic generation database and associated algorithm may store versions of a variety of graphic selections, thus embedding the graphic selections within the system. This is useful for routinely and easily applying specific graphics to two or more segmented features (for example liver or fat cells, as described above). Alternatively, or additionally, a dedicated graphics AI model may be trained so that when deployed, a computing device on which the graphics AI model is operating may process an intermediary image comprising: i) a single one segmented boundary feature; or ii) two or more segmented boundary features, thereby automatically identifying a most suitable graphic for application onto the segmented boundary feature(s). The graphics AI model may employ one or more image search functionalities and/or may be triggered by text inputs.

In a further aspect of the invention, one or both of the intermediary image comprising i) a single segmented boundary feature; or ii) two or more segmented boundary features and the graphic feature image, upon which is applied one or more graphics, may additionally comprise text annotations, identifying the segmented boundary feature or features. Such text annotations on both the intermediary image and the graphic feature image may be toggled on/off by an operator, as desired, for example, by using touchscreen features on the user interface (such as the display screen) or by using ancillary control devices. FIGS. 9 and 10 show examples of such annotation.

In a further embodiment of the invention there is provided a step, after applying a graphic onto the i) a single segmented boundary feature; or ii) two or more segmented boundary features, thereby forming a graphic feature image, of tracking displacement of at least one aspect of the graphic feature image using a tracking algorithm, to direct adjustments to the graphic feature image within the segmented boundary features. Such adjustments to the segmented boundary features create a visual of dynamic motion of the graphic feature image. In this way, the applied graphics may be seen, by an operator/user/viewer, as a non-static, more realistic representation of the segmented boundary features.

Tracking displacement may be achieved by a variety of different means and the present invention is not intended to be limited to any particular one. As one or more graphics are applied to segmented ultrasound images (acquired in some embodiments of the invention, in real time), it is possible to select and track features, such as for example an anatomical feature or artifact moving due to an anatomical feature moving or a subject being scanned moving, across multiple frames of ultrasound imaging data, to determine a delta or change in that anatomical feature or artifact and thereafter to apply that change, for example using a tracking algorithm, to direct adjustments to the graphic feature image within the segmented boundary features. Those directed adjustments create "movement" in the graphic, applied over the segmented boundary features.

Such motion tracking may be achieved by selecting specific anatomical features or artifacts (one or more) to track, image over image, using a tracking algorithm, or using a dedicated camera or gyroscope system. In some aspects, anatomical features or artifacts may be tracked from frame to frame using a feedback mechanism, across multiple ultrasound images, even if the anatomical features or artifacts morph or otherwise change in visual appearance due to patient/subject movement or movement of an ultrasound probe of the ultrasound imaging system. An annotation indicative of a first location of an identified anatomical feature or artifact is identified in a first ultrasound image and then an adjusted annotation based on a second location of the same identified anatomical feature or artifact is identified in a second ultrasound image.

As such, tracking illustrates a plurality of dynamic states, and the ultrasound images show movement, velocity, or other changes in the patient/subject and/or probe. In an embodiment, a multivariate regression model may be used to determine a relationship between relative positions of one or more identified anatomical features or artifacts in the plurality of images showing a first condition and relative positions of the one or more identified anatomical features or artifacts in the plurality of images showing a second condition. In an embodiment, the determined relationship is used to predict positions of the one or more identified anatomical features or artifacts in another dataset. Given positions of the one or more identified anatomical features or artifacts in the acquired plurality of images showing the first condition and the determined relationship, positions of the one or more identified anatomical features or artifacts in the acquired plurality of images showing the second condition may be predicted. Such a prediction may be used to shift the graphic as applied to each ultrasound image frame, comprising the at least two segmented boundary features.

By way of example, a speckle tracking algorithm may be applied to direct movement of graphics, frame over frame, thereby to create visual effect of movement of the graphic feature image. A speckle tracking algorithm applies a statistical analysis of pixels (direction movement frame as compared to frame) which provides a vector (direction and velocity) and creates "movement" for image layers. In ultrasound imaging, speckle noise occurs as a result of interference of scattered echo signals reflected from an object, such as an organ. The speckle noise or speckle appears as a granular grayscale pattern on an ultrasound image. Generally, speckle noise may degrade image quality since the speckles obtained from different angles are incoherent, but within the scope of the invention, this naturally occurring speckle pattern is used to advantage, as a trackable marker. On an ultrasound image, for each anatomical feature being scanned, there is a naturally occurring speckle pattern. While each pattern is random, various parts of an anatomical feature being scanned will comprise its own unique speckle pattern (also called patterns, features, or fingerprints) that allows the region to be tracked. The speckle pattern is relatively stable, at least from one frame to the next and in post processing this can be tracked consecutively frame to frame and ultimately resolved into angle-independent two-dimensional (2D) sequences. These sequences provide both quantitative and qualitative information regarding tissue deformation and motion. Within an ultrasound image of an anatomical feature, a defined area "kernel" can be defined, and as this speckle pattern is relatively stable, the kernel can be recognised in the next frame, within a larger search area, by a "best match" search algorithm. There are a variety of search algorithms, the most used commonly used is "sum of absolute differences", shown to be similarly accurate as cross-correlation, which is an alternative. The movement of the kernel across the ultrasound image can thus be tracked, independent of the beam angle, and in two dimensions.

There are a variety of techniques known and employed in the art to employ speckle tracking algorithms in the field of cardiology which techniques were used and adapted to a variety of other applications including musculoskeletal applications. These widely available speckle tracking techniques and associated algorithms may be adapted for use within the scope of the present invention. There are a variety of methods employed in speckle-tracking including one based on block matching, where the region of interest (ROI) is divided into a number of smaller subregions (blocks) that are then individually matched to determine their corresponding locations in subsequent ultrasound frames. The blocks are typically allowed to move with the tissue or anatomical feature being scanned but can also remain stationary and instead measure the "flow" of tissue through the block, which has the advantage of being able to track motion even if tissue or anatomical feature leaves the scanned field of view. Another approach that has been used for speckle-tracking involves warping the entire ROI to match subsequent frames, referred to as "image registration". This warping is often achieved through a linear (affine) transformation of the image (i.e., translation, rotation, scaling, and shear).

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

The system of the present invention uses a transducer (a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

A user input device may comprise one or more of a touchscreen, a keyboard, a mouse, a trackpad, a motion sensing camera, or other device configured to enable a user to interact with and manipulate data within image processing system. In one example, user input device may enable a user to make a selection of an ultrasound image to use in training an AI model, or for further processing using a trained AI model. A display device may include one or more display devices utilizing virtually any type of technology. In some embodiments, display device may be part of a multi-purpose display device or may comprise a computer monitor, and in both cases, may display ultrasound images. A display device may be combined with processor, non-transitory memory, and/or user input device in a shared electronic device, or there may be peripheral display devices which may comprise a monitor, touchscreen, projector, or other display device known in the art, which may enable a user to view ultrasound images produced by an ultrasound imaging system, and/or interact with various data stored in non-transitory memory.

In various embodiments, a multi-purpose electronic devices/display devices may be, for example, a laptop computer, a tablet computer, a desktop computer, a smart phone, a smart watch, spectacles with a built-in display, a television, a bespoke display or any other display device that is capable of being communicably connected to an ultrasound probe. Multi-purpose electronic devices/display devices may host a screen (such as shown in FIGS. 6 and 8), and may include a processor, which may be connected to a non-transitory computer readable memory storing computer readable instructions, which, when executed by the processor, cause the display device to provide one or more of the functions of the system (such system comprising at least one multi-purpose electronic device and at least probe). Such functions may be, for example, the receiving of ultrasound data that may or may not be pre-processed; scan conversion of received ultrasound data into an ultrasound image; processing of ultrasound data in image data frames; the display of a user interface; the control of a probe and the display of an ultrasound image on the screen. Such a screen may comprise a touch-sensitive display (e.g., touchscreen) that can detect a presence of a touch from the operator on screen and can also identify a location of the touch in screen. The touch may be applied by, for example, at least one of an individual's hand, glove, stylus, or the like. As such, the touch-sensitive display may be used to receive an input, for example, indicating the presence or absence of text or annotations on a graphic feature image. The screen and/or any other user interface may also communicate audibly. Multi-purpose electronic devices/display devices may be configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory within the multi-purpose electronic devices/display devices may be computer readable data which may be used by processors within multi-purpose electronic devices/display devices, in conjunction with the computer readable instructions within multi-purpose electronic devices/display devices 801 and 901, to provide the functions of the system. Such computer readable data may include, for example, settings for ultrasound probe, such as presets for acquiring ultrasound data and settings for a user interface displayed on screens. Settings may also include any other data that is specific to the way that the ultrasound probe operates or that multi-purpose electronic devices/display devices operate.

Referring to FIG. 1, there is shown a flowchart diagram of a method, generally indicated at 100, of new image frame acquisition of an anatomical feature, processing against an AI model to identify and segment boundaries, in whole or part of i) a single feature; or ii) two or more features, on the new ultrasound image, thereby creating i) a single segmented boundary feature or ii) two or more segmented boundary features, applying a graphic onto the at segmented boundary feature or features, thereby forming a graphic feature image and generating an output image, on the screen, comprising the graphic feature image, according to at least one embodiment of the present invention. At 102, the ultrasound imaging system (e.g., as referred to in FIGS. 13 and 14), may acquire ultrasound imaging data in the form of an imaging frame. For example, a user may operate an ultrasound scanner (hereinafter "scanner", "probe", or "transducer" for brevity) to capture images of a patient. The ultrasound frames (B-mode) may be acquired by acquiring a series of a images (with a frame each containing a sequence of transmitted and received ultrasound signals) of different views of a region of interest.

Further, at step 103, a new ultrasound imaging frame may optionally be pre-processed and/or augmented. In some embodiments, an optional pre-processing act may be performed on the new ultrasound image frame to facilitate improved performance and/or accuracy when training the machine learning (ML) algorithm. For example, it may be possible to pre-process the ultrasound imaging frame through a high contrast filter to reduce the granularity of greyscale on the ultrasound image. Additionally, or alternatively, it may be possible to reduce scale of the ultrasound image frame prior to providing the ultrasound image frame for processing through the AI model at step 104. Reducing the scale of ultrasound image frame as a preprocessing step may reduce the amount of image data to be processed, and thus may reduce the corresponding computing resources required. Various additional or alternative pre-processing acts may be performed. For example, these acts may include data normalization to ensure that the various ultrasound imaging frame has the dimensions and parameters which are optimal for processing through the AI model.

At step 104, the new ultrasound imaging frame/image data is processed with an AI model to identify and segment boundaries of a single anatomical feature or two or more features within ROI, in whole or part. The product of the AI model is an intermediary image comprising segmented boundaries on or around one feature or two or more segmented features upon which graphics are subsequently applied. Optionally, the AI model, at this step, may apply labels, annotations, text, captions to the segmented boundary features (such as shown in FIGS. 9 and 10 wherein annotations are applied to intermediary images 904 and 1004). At step 108, graphics are applied to the single segmented boundary feature or the at least two segmented boundary features creating a graphic feature image. There may be a plurality of segmented boundary features, in accordance with the anatomy within the ROI. The same or different graphics may be applied to the segmented boundary features. At step 110, an output comprising the graphic feature image is displayed, for example on a screen of a multi-purpose electronic display device such as 1350 in FIG. 13. Graphic feature images are exemplified in FIGS. 9 and 10 as 906 and 1006. A user viewing the display of graphic feature image may take certain actions pertaining to the image, including but not limited to manipulating the size of the image, zooming in or out of the image, saving the image, adding text or annotations to the image, and/or selecting the image for inclusion in a multimedia product. For example, in FIG. 10, annotations are added to intermediary image 1004 (here shown as abbreviations L, K, SP, GB etc.) and also to graphic feature image 1006 (see "L" which identifies the liver graphic). At step 112, direction is provided to repeat steps 102-110 for additional images.

Referring to FIG. 2, there is shown a flowchart diagram of a method, generally indicated at 200, of providing optional text overlays onto a displayed graphic feature image. At step 201, which is the equivalent to step 110 in FIG. 1, a graphic feature image is displayed. The optional provision of one or more text additions on, associated with or directed to each of the segmented boundary feature/features shown as part of the graphic feature image is at step 202, such additions being either automatically generated by a graphic generation device and associated algorithm or may be generated by user selections, such as by manual inputs. At step 203, an updated graphic feature image, comprising text/annotations is displayed. Such text annotations on the graphic feature image may be toggled on/off by an operator at step 204, as desired, for example, by using touchscreen features on the user interface (such as the display screen) or by using ancillary control devices. As noted above, FIG. 10 illustrates annotations which may be optionally provided to one or both of the intermediary (segmented) image 1004, which is the output of the AI model and/or to the graphic feature image 1006 upon which the graphics/textures have been applied.

Referring to FIG. 3, shown there generally is a schematic diagram of a method, generally indicated at 300 of, after applying a graphic onto the segmented boundary feature/features, forming a graphic feature image (such as the output of steps 108 in FIG. 1), thereafter tracking displacement at step 301 of at least one aspect of the graphic feature image using a tracking algorithm. At step 302 at least one segmented boundary feature or at least one graphic feature is adjusted, based upon a tracked displacement output of the tracking algorithm. An updated and adjusted graphic feature image is displayed at step 304.

For greater clarity, motion tracking is further illustrated generally at 400 in FIG. 4, in which a first graphic feature image frame (such as an output of step 108 in FIG. 1), is received at 401 and which is then processed at step 402 to find therein at least one identifiable landmark, marker or point at position "P". In a subsequent graphic image frame, at step 403, corresponding $P^1$ is identified so that, at step 404, motion or displacement between P and P1 may be correlated to motion between the first graphic feature image frame and the subsequent or following graphic feature image frame. Graphic motion, and its manifestation on sequential graphic feature images, is further illustrated in FIGS. 17A, 17B and 17C.

Figure 5:
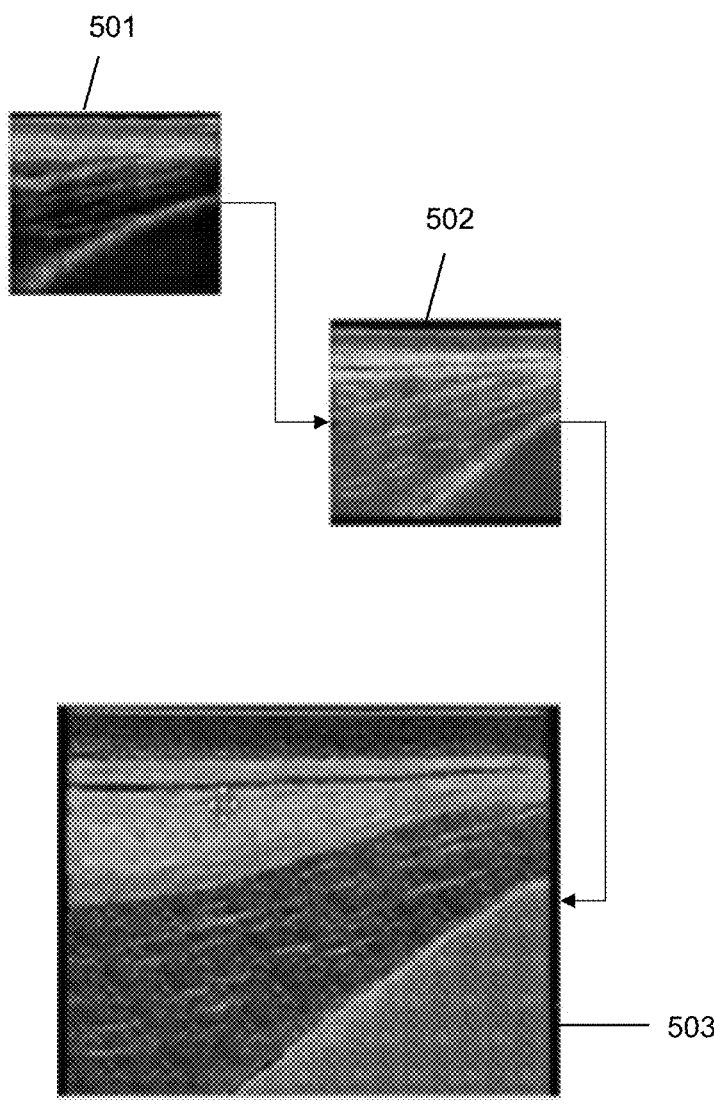
FIG. 5 is a schematic of the progression of images, from a B-mode ultrasound image, to a subsequently created segmented image to a graphic feature image, for an aesthetics application (facial scan), according to an embodiment of the present invention.

A schematic of the progression of images, created by the method of the invention is shown generally at 500 in FIG. 5, from a B-mode ultrasound image acquired from an ultrasound scanner 501, to a subsequently created intermediate segmented image 502 (by processing B-mode image 501 through AI model as set out in step 104 in FIG. 1), to a graphic feature image 503 (by applying graphics to intermediate segmented image 502 as set out in step 108 in FIG. 1). In this example, B-mode image 501 is a facial scan, useful in aesthetic treatments and applications, wherein intermediate segmented image 502 comprises a delineation of a plurality of boundaries of features which are clinically useful to delineate and easily view during aesthetic procedures. Graphic feature image 503 shows graphics applied to areas within those same segmented boundaries. These segmented boundaries and graphic features are illustrated best in FIG. 6.

FIG. 6 is a schematic of an exemplary user interface display shown generally at 600, showing two image parts: on the left side 602 of image display area 601 a facial aesthetics image corresponding to intermediate segmented image 502 comprising the segmented boundary features and on the right side 603 of image display area 601, a facial aesthetics image corresponding to the graphic feature image 503, with graphics applied onto the various segmented boundary features. Segmented image (left side 602) and corresponding applied graphics image (right side 603) illustrate, as follows: segmented superficial fascia 604 applied with superficial fascia graphic 605; segmented subcutaneous fat 606 applied with subcutaneous fat graphic 607; segmented fat 608 applied with fat graphic 609; segmented deep fascia 610 applied with deep fascia graphic 611; segmented muscle 612 applied with muscle graphic 613; and segmented bone 614 applied with bone graphic 615. It is to be understood that an interface display, such as at 600, may additionally or alternatively show a B-mode image or other type of acquired ultrasound image frame, a segmented (intermediate) image and/or a graphic image, at the same time or interchangeably. A user may control such viewing and interchange of images just as a user may control the viewing of text overlays and annotations on the segmented (intermediate) image and/or a graphic image. Exemplary text overlay is shown in FIG. 6 as S. Facia, SubCFat, D. Facia, Muscle, Bone, and Fat).

Interface screen 600 may additionally comprise controls and guides including but not limited to: imaging mode selector 616, freeze button 617, video icon 618, screen capture icon 619, tools icon at 620 and texture mode selector, enabling the segmentation and graphic application, of the present invention, at 621.

A schematic of the progression of images, created by the method of the invention is shown generally at 700 in FIG. 7, from a B-mode ultrasound image 702 acquired from an ultrasound scanner 1331, to a subsequently created intermediate segmented image 704 (by processing B-mode image 702 through AI model as set out in step 104 in FIG. 1), to a graphic feature image 706 (by applying graphics to intermediate segmented image 704 as set out in step 108 in FIG. 1). In this example, B-mode image 702 is a neck scan, wherein intermediate segmented image 704 comprises a delineation of the segmented boundaries of each of: trachea 708, thyroid gland 710, esophagus 712, carotid artery 714, sternocleidomastoideole (SCM) 716, strap muscle 718, carotid artery 720, and longus colli muscle (LCM) 722. It is to be understood that every feature within a B-mode need not necessarily be segmented. Such non-segmented features may remain as a B-mode visual on both the intermediary image (704) and graphic feature image (706). It is clearly shown in FIG. 7 that a plurality of regions are displayed as B-mode (for example above strap muscle/strap muscle graphic 718/738). Graphic feature image 706 illustrates particular graphic features applied within each of the above-noted segmented boundaries. Trachea graphic 728 is applied within trachea (segmented boundary) 708, thyroid graphic 730 is applied within thyroid gland (segmented boundary) 710, esophagus graphic 732 is applied within esophagus (segmented boundary) 712, carotid artery graphic 734 is applied within carotid artery (segmented boundary) 714, sternocleidomastoideole graphic 736 is applied within sternocleidomastoideole (segmented boundary) 716, strap muscle graphic 738 is applied withing strap muscle (segmented boundary) 718, carotid artery graphic 740 is applied within carotid artery (segmented boundary) 720, and longus colli muscle graphic 742 is applied withing longus colli muscle (segmented boundary) 722. It is to be understood that every feature within a B-mode image, such as 501 in FIG. 5, 702 in FIG. 7, 902 in FIG. 9, 1002 in FIG. 10 need not necessarily be segmented. Such non-segmented features may remain as a black/grey/white B-mode visual, even within a graphic feature image (such as, for example, the anatomy above the strap muscle graphic 738 in graphic feature image 706, FIG. 7 and the anatomy above liver graphic 928 in graphic feature image 906, FIG. 9). There is flexibility and latitude in the application of graphics which are most useful in the context of each particular use.

Figure 7:
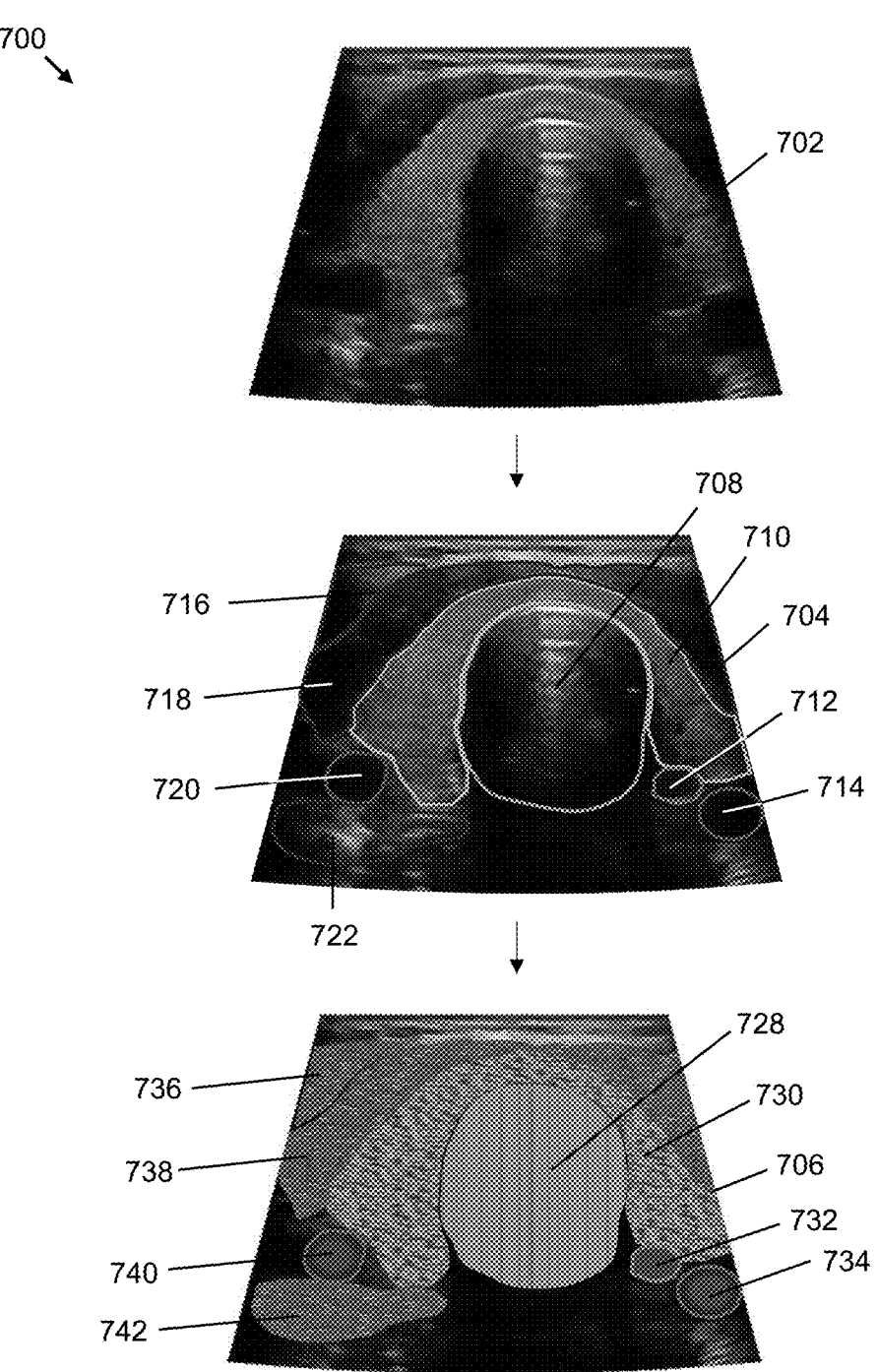
FIG. 7 is a schematic of the progression of images, from a B-mode ultrasound image, to a subsequently created segmented image to a graphic feature image, for a thyroid application (neck scan), according to an embodiment of the present invention.

FIG. 8 is a schematic of an exemplary user interface display shown generally at 800, showing two image parts: on the left side 802 of image display area 801 a neck/thyroid image corresponding to intermediate segmented image 704 comprising the segmented boundary features and on the right side 803 of image display area 801, a neck/thyroid image corresponding to the graphic feature image 706, with graphics applied onto the various segmented boundary features as described in FIG. 7. In this way, a user can see both a segmented view and graphics view for ease in side-by-side understanding, identification and the relative positioning of anatomical features. In other embodiments, an exemplary user interface display may comprise a B-mode image on one side and a graphic feature image on another side, for comparison. In yet another embodiment, an exemplary user interface display may comprise a B-mode image on one side and a segmented (intermediary) image on another side, for comparison, prior to the application of graphics. In yet another embodiment, an exemplary user interface display may comprise all three of a B-mode image, a segmented (intermediary) image and a graphic feature image, for comparison. In yet another embodiment, an exemplary user interface display may comprise a segmented (intermediary) image and a graphic feature image, for comparison, and at least one of these images may be overlayed with text or other annotations identifying the segmented anatomical features.

Interface screen 800 may additionally comprise controls and guides including but not limited to: imaging mode selector 816, freeze button 817, video icon 818, screen capture icon 819, tools icon at 820 and texture mode selector, enabling the segmentation and graphic application, of the present invention, at 821.

A schematic of the progression of images, created by the method of the invention is shown generally at 900 in FIG. 9, from a B-mode ultrasound image 902 acquired from an ultrasound scanner 1331, to a subsequently created intermediate segmented image 904 (by processing B-mode image 902 through AI model as set out in step 104 in FIG. 1), to a graphic feature image 906 (by applying graphics to intermediate segmented image 904 as set out in step 108 in FIG. 1). In this example, B-mode image 902 is an abdominal scan, wherein intermediate segmented image 904 comprises a delineation of boundaries of each of: superior mesenteric vein/splenic vein confluence 907, liver (left lobe) 908, spleen 910, kidney (upper pole) 912, superior mesenteric artery 914, vertebrae (lumbar) 916, aorta 918, pancreas 920 and bowel loops 922. Graphic feature image 906 illustrates particular graphic features applied within each of the above-noted segmented boundaries. Superior mesenteric vein/splenic vein confluence graphic 927 is applied within superior mesenteric vein/splenic vein confluence (segmented boundary) 907, liver (left lobe) graphic 928 is applied within liver (segmented boundary) 908, spleen graphic 930 is applied within spleen (segmented boundary) 910, kidney (upper pole) graphic 932 is applied within kidney (segmented boundary) 912, superior mesenteric artery graphic 934 is applied within superior mesenteric artery (segmented boundary) 914, vertebrae (lumbar) graphic 936 is applied within vertebrae (segmented boundary) 916, aorta graphic 938 is applied with aorta (segmented boundary) 918, pancreas graphic 940 is applied within pancreas (segmented boundary) 920, and bowel loops graphic 942 is applied within bowel loops (segmented boundary) 922.

Intermediate segmented images such as 904, may additionally display text, annotation, abbreviation, symbols, legends or the like on one or more segmented anatomical features. As shown in FIG. 9, there are abbreviations referring to each segmented anatomical feature as follows:

B=Bowel loops

P=Pancreas

SP=Spleen

SM=Superior mesenteric vein/splenic vein confluence

S=Superior mesenteric artery

A=Aorta

V=Vertebrae (Lumbar)

K=Kidney (upper pole)

A schematic of the progression of images, created by the method of the invention is shown generally at 1000 in FIG. 10, from a B-mode ultrasound image 1002 acquired from an ultrasound scanner 1331, to a subsequently created intermediate segmented image 1004 (by processing B-mode image 1002 through AI model as set out in step 104 in FIG. 1), to a graphic feature image 1006 (by applying graphics to intermediate segmented image 1004 as set out in step 108 in FIG. 1). In this example, B-mode image 1002 is another abdominal scan, different from that in FIG. 9, wherein intermediate segmented image 1004 comprises a delineation of boundaries of: gall bladder 1008, inferior vena cava 1010, lumbar vertebrae/spine 1012, kidney 1014 and liver 1016. Graphic feature image 1006 illustrates particular graphic features applied within each of the above-noted segmented boundaries. Gall bladder graphic 1028 is applied within gall bladder (segmented boundary) 1008. Inferior vena cava graphic 1030 is applied within inferior vena cava (segmented boundary) 1010. Lumbar vertebrae/spine graphic 1032 is applied within lumbar vertebrae/spine (segmented boundary) 1012. Kidney graphic 1034 is applied within kidney (segmented boundary) 1014. Liver graphic 1036 is applied within liver (segmented boundary) 1016. In addition, an annotation "L" shown at 1038 is applied, further designating the graphic applied region as the liver.

As shown in FIG. 10, there are abbreviations referring to each segmented anatomical feature as follows:

L=Liver

GB=Gall Bladder

IVC=Inferior Vena Cava

K=Kidney

SP=Spine/Lumbar Vertebrae

The present invention further provides a method of selecting a graphic/texture to apply onto a single segmented feature or onto two or more segmented features which comprises automatically measuring one or one dimensions defined by the segmented feature or segmented features (at least one segmented feature or part thereof) to create a defined measurement, using the defined measurement to select a graphic to apply on the segmented feature, segmented features and/or a part thereof. In one embodiment of the invention, both the measurement and graphic selection is automatic and occurs without user intervention. In some embodiments of the invention, calipers are automatically placed at two or more points on i) the single segmented feature or ii) two or more segmented features (or parts thereof) for the purpose of auto-measurement acquisition. In some embodiments of the invention, what a defined measurement is, in connection with the anatomical feature segmented and/or in connection with the ROI, determines what specific graphic/texture is selected and applied and how it appears in the concomitant graphic feature image. In some embodiments of the invention, a defined measurement (1) may be continually updated, and an updated graphic/texture is applied, and an updated graphic feature image is created based upon the updated defined measurement (2)

and as such the change to the defined measurement ($\Delta^1$-$\Delta^2$). If a defined measurement changes over time T, the applied graphic/texture may change from time $T^1$ to $T^2$.

The application of a specific graphic/texture based upon a defined measurement (or defined gradient of measurements) may be employed in a variety of clinical and educational applications. For example, as described below, in FIGS. 15 and 16, wherein a defined measurement is the automatic measurement of crown rump length, a fetal age-appropriate graphic (related to the output CRL measurement) is algorithmically selected and applied to a single segmented feature (i.e., the fetus). Similarly, wherein a defined measurement is bladder volume (V), acquired from an intermediary segmented image of a bladder, a fullness appropriate graphic (related to actual bladder volume, i.e., pre-void residual bladder volume, of the patient being scanned), is algorithmically selected and applied to or around the segmented feature (i.e., the bladder). For the bladder, by way of example, a fuller bladder (higher cc) may be graphically shown as a deeper yellow while a less full bladder (lower cc) may be graphically shown as a lighter yellow. A legend of such color gradients, and the correlation to pre-void residual bladder volume may be provided on a user interface display (for example a cc numerical scale related to a gradient of color change).

Figure 15:
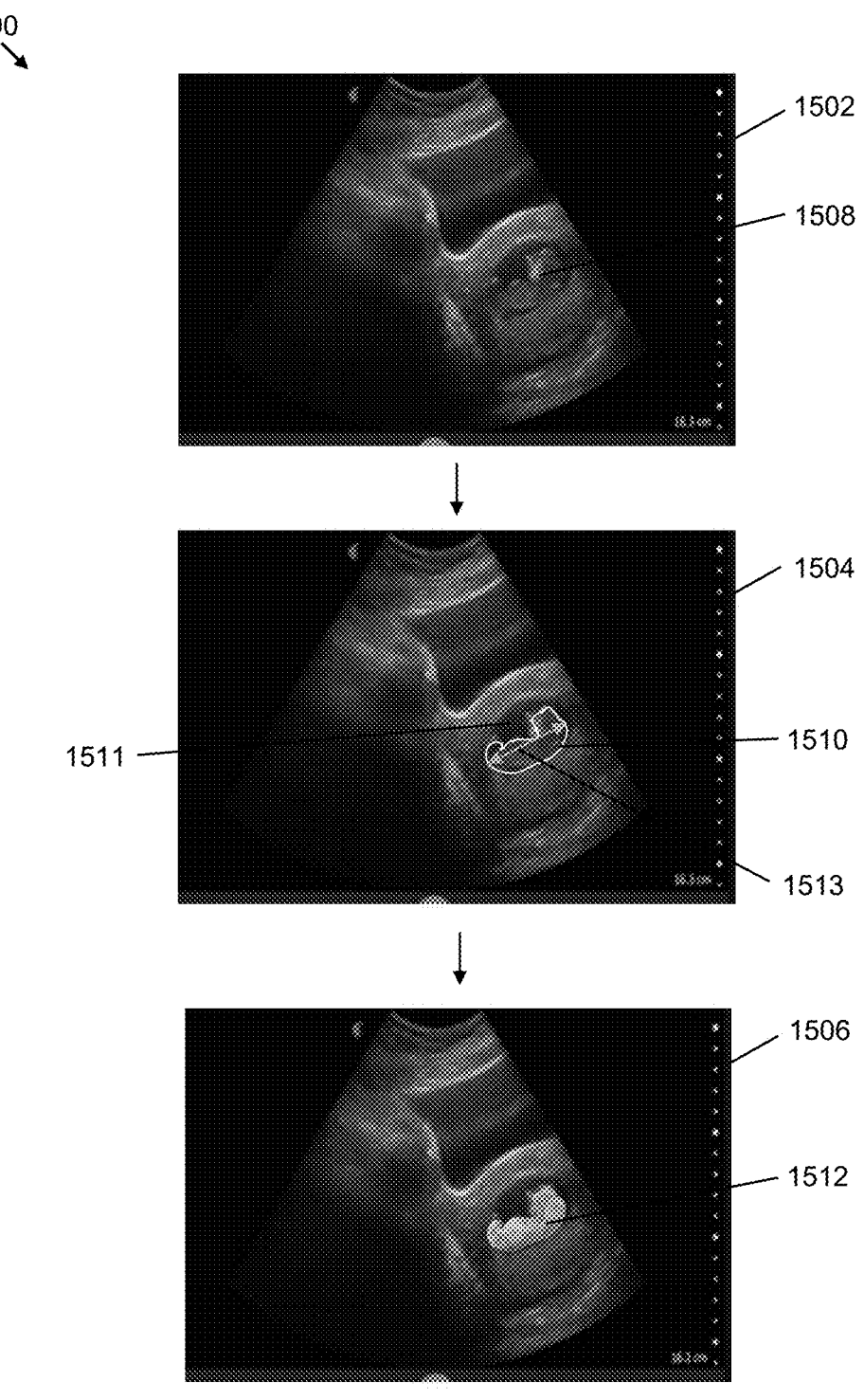
FIG. 15 is a schematic of the progression of images, from a B-mode ultrasound image, to a subsequently created segmented image to a graphic feature image, for an obstetrics application (fetal scan at a gestational age within first trimester), according to an embodiment of the present invention.

A schematic of the progression of images, created by the method of the invention is shown generally at 1500 in FIG. 15, from a B-mode ultrasound image 1502 acquired from an ultrasound scanner 1331, to a subsequently created intermediate segmented image 1504 (by processing B-mode image 1502 through AI model as set out in step 104 in FIG. 1), to a graphic feature image 1506 (by applying graphics to intermediate segmented image 1504 as set out in step 108 in FIG. 1). In this example, the B-mode image 1502 is from a fetal ultrasound scan, within a first trimester, showing fetus 1508, within amniotic fluid 1511, wherein intermediate segmented image 1504 comprises a delineation of a single boundary around a fetus 1508, thus showing an example of a single feature and a single boundary delineation. In this embodiment, in intermediate segmented image 1504, and after fetus 1508 has been segmented, as shown, a crown-rump length (CRL) a measurement of the fetus/embryo along its longest axis, may be i) automatically determined; ii) automatically used to assess a gestational age/approximate gestational age of the fetus; and iii) used to apply a gestational age specific graphic within the segmented boundary. CRL is shown in FIG. 15 as 1510. With that, graphic 1512, which is visually representative of the approximate gestational age suggested by the CRL according to known translation charts, is automatically applied.

Figure 16:
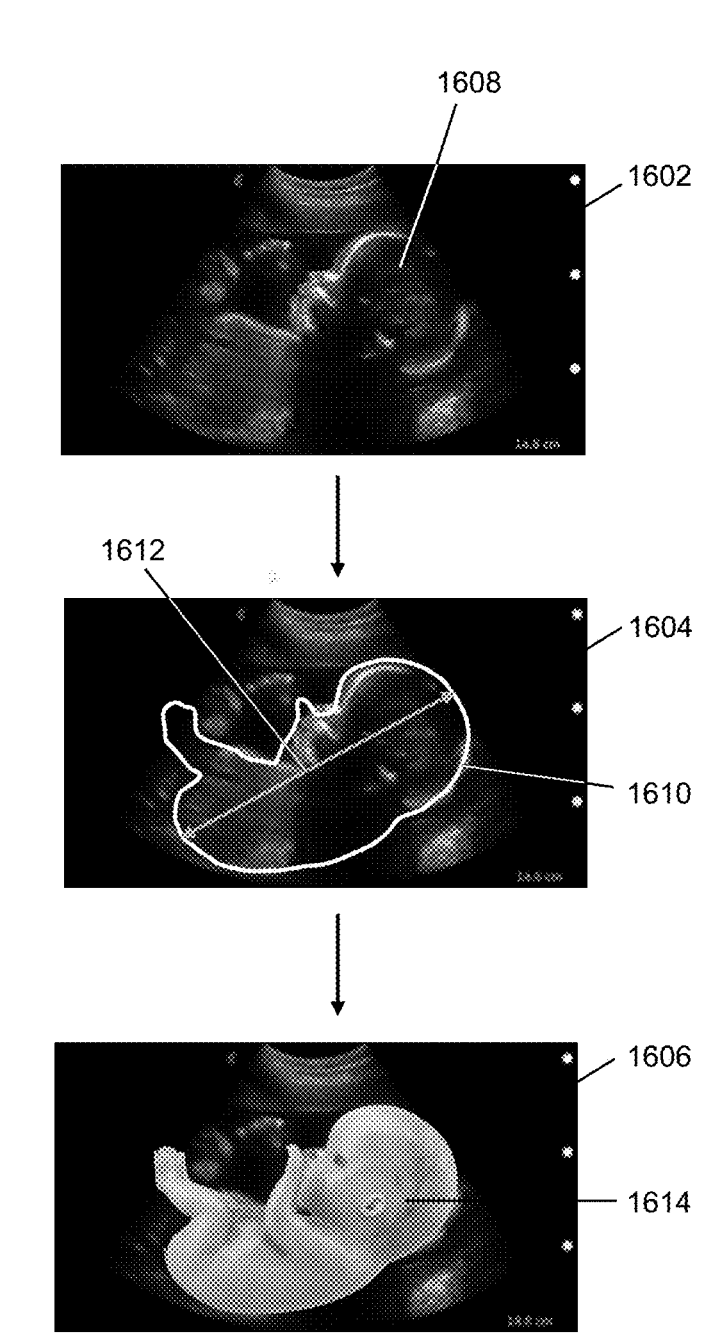
FIG. 16 is a schematic of the progression of images, from a B-mode ultrasound image, to a subsequently created segmented image to a graphic feature image, for an obstetrics application (fetal scan at a gestational age within second trimester), according to an embodiment of the present invention.

A schematic of the progression of images, created by the method of the invention is further shown generally at 1600 in FIG. 16, from a B-mode ultrasound image 1602 acquired from an ultrasound scanner 1331, to a subsequently created intermediate segmented image 1604 (by processing B-mode image 1602 through AI model as set out in step 104 in FIG. 1), to a graphic feature image 1606 (by applying graphics to intermediate segmented image 1604 as set out in step 108 in FIG. 1). In this example, the B-mode image 1602 is from a fetal ultrasound scan, within a second trimester, showing fetus 1608, wherein intermediate segmented image 1604 comprises a delineation of a single boundary around a fetus 1608, thus showing another example of a single feature and a single boundary delineation. In this embodiment, in intermediate segmented image 1604, and after fetus 1608 has been segmented, as shown by encircling line 1610, a crown-rump length (CRL) a measurement of the fetus/embryo along its longest axis, may be i) automatically determined; ii) automatically used to assess a gestational age/approximate gestational age of the fetus; and iii) used to apply a gestational age specific graphic within the segmented boundary. CRL is shown in FIG. 16 as 1612. With that, graphic 1614, which is visually representative of the approximate gestational age suggested by the CRL, is automatically applied.

In various embodiments, different representative fetus graphics may be used for different gestational ages, and the selection of the representative fetus graphic may have different time granularity. For example, the selection of the fetus graphic may be to the closest month of gestational age or the closest week of gestational age, as determined by the gestational age suggested by the automated CRL measurement.

In various embodiments, a variety of means to segment an ultrasound image may be used. For example, segmentation may be performed by dividing it into multiple parts or regions that belong to the same class. This task of clustering is based on specific criteria, for example, color or texture and is referred to as pixel-level classification. This involves partitioning images into multiple segments or objects using techniques including, but not limited to 1) thresholding, wherein a threshold value is set, and all pixels with intensity values above or below the threshold are assigned to separate regions; 2) region growing, wherein an ultrasound image is divided into several regions based on similarity criteria. This segmentation technique starts from a seed point and grows the region by adding neighboring pixels with similar characteristics; 3) edge-based segmentation wherein segmentation techniques are based on detecting edges in the ultrasound image and these edges represent boundaries between different regions that are detected using edge detection algorithms; 4) clustering, wherein groups of pixels are clustered based on similarity criteria. These criteria can be color, intensity, texture, or any other feature; 5) active contours, also known as snakes, wherein curves that deform are used to find the boundary of an object in an image. These curves are controlled by an energy function that minimizes the distance between the curve and the object boundary; 6) deep learning-based segmentation, such as by employing Convolutional Neural Networks (CNNs), which employ a hierarchical approach to image processing, where multiple layers of filters are applied to the input image to extract high-level features, the training of which is described herein in FIGS. 11 and 12.

Figure 11:
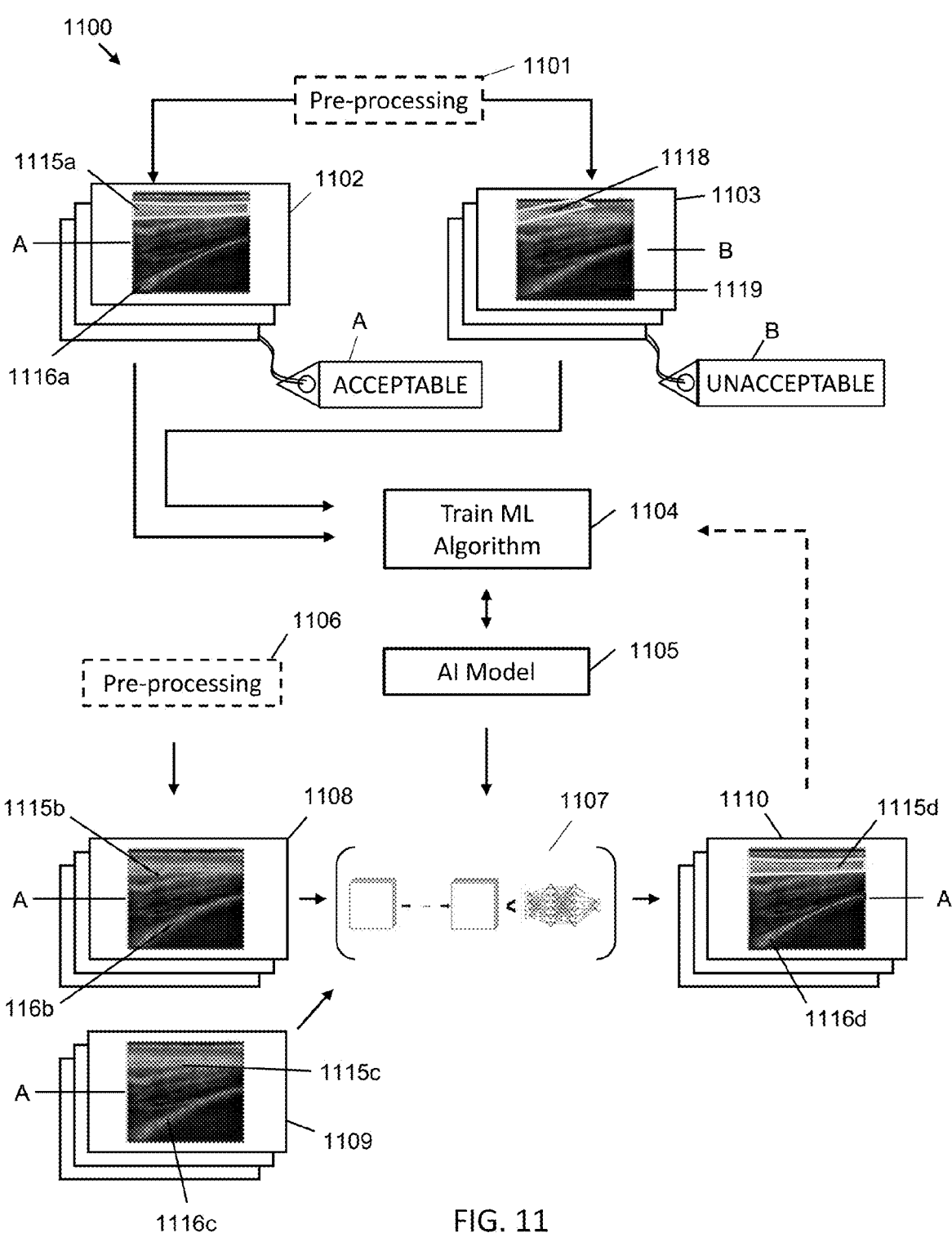
FIG. 11 is a schematic diagram of the training and deployment of an AI model, according to an embodiment of the present invention.

Referring to FIG. 11, shown there generally at 1100 is a schematic diagram of a training and deployment of an AI model 1105. According to an embodiment of the present invention, there is shown a method of training a neural network 1107 to so that when the AI model is deployed, a computing device identifies and segments boundaries of features, in whole or part. Specifically, during use and deployment, neural network 1107 identifies, in a new ultrasound image, optimal feature boundary delineation, based upon the ROI in an ultrasound image frame.

For training, a number of ultrasound frames of a ROI (in whole view, from varying perspectives and parts thereof) may be acquired using an ultrasound scanner (hereinafter "scanner", "probe", or "transducer" for brevity). The ultrasound frames may be acquired by fanning a series of a planes (with a frame each containing a sequence of transmitted and received ultrasound signals), through an angle and capturing a different ultrasound frame at each of a number of different angles. During the scanning, the scanner may be held steady by an operator of the scanner while a motor in the head of the scanner tilts the ultrasonic transducer to acquire ultrasound frames at different angles. Additionally, or alternatively, other methods of acquiring a series of ultrasound frames may be employed, such as using a motor to translate (e.g., slide) the ultrasonic transducer or rotate it, or manually tilting, translating or rotating the ultrasound scanner.

The AI model if preferably trained with a robust selection of images of varying views. For example, these different views may include transverse plane views of a ROI, including views from different angles that combine any of a sagittal plane view, a coronal plane view, or a transverse plane view. In these embodiments, the scanner may be placed in an arbitrary orientation with respect to the ROI, provided that the scanner captures at least a portion of the ROI.

In some embodiments, ultrasound scans of a ROI, for training, may be acquired from medical examinations. During the scans, images may be obtained; however, for training of the AI model of the invention, non-clinically useful or acceptable images may also be used.

Referring still to FIG. 11, training ultrasound frames (1102 and 1103) may include ultrasound frames with features that are tagged as acceptable (A) and representative of images comprising one or more anatomical features which are segmented and most advantageously depict two or more segmented boundaries of a desired ROI or alternatively are tagged respectively as unacceptable (B) and unrepresentative of such division and segmentation. By way of example, in ultrasound frame 1102, which is marked as acceptable, there is provided two segmented boundary features 1115a and 1116a, which are marked as correctly and at least adequality segmented. Conversely, ultrasound frame 1103, of the same ROI as ultrasound frame 1102, is marked as unacceptable, due to the fact that the two segmented boundary features 1118 and 1119, are incorrect and at least non-adequality segmented.

Both the training ultrasound frames labeled as Acceptable and Unacceptable, for each particular ROI (whole or part), may themselves be used for training and/or reinforcing AI model 1105. This is shown in FIG. 12 with tracking lines from both 1011 to training algorithm step 1210. As such, ultrasound frame 1103 may be employed for training as an unacceptable image.

In some embodiments, an optional pre-processing act 1101 may be performed on the underlying ultrasound image frames 1102 and 1103 to facilitate improved performance and/or accuracy when training the machine learning (ML) algorithm. For example, it may be possible to pre-process the ultrasound images 1102 and 1103 through a high contrast filter to reduce the granularity of greyscale on the ultrasound images 1102 and 1103.

Additionally, or alternatively, it may be possible to reduce scale of the ultrasound images 1102 and 1103 prior to providing the ultrasound images 1102 and 1103 to the training algorithm step 1104. Reducing the scale of ultrasound images 1102 and 1103 as a preprocessing step may reduce the amount of image data to be processed during the training act 1104, and thus may reduce the corresponding computing resources required for the training act 1104 and/or improve the speed of the training act 1104.

Various additional or alternative pre-processing acts may be performed in act 1101. For example, these acts may include data normalization to ensure that the various ultrasound frames 1102 and 1103 used for training have generally the same dimensions and parameters.

Referring still to FIG. 11, the various training frames 1102 and 1103 may, at act 1104, be used to train a ML algorithm. For example, the various training ultrasound frames 1102 and 1103, may be inputted into deep neural network 1107 that can learn how to predict boundaries of features in new ultrasound images as compared to all trained and stored images.

The result of the training may be the AI model 1105, which represents the mathematical values, weights and/or parameters learned by the deep neural network to predict segmented boundaries of features, within a ROI, in whole or part. The training act 1104 may involve various additional acts (not shown) to generate a suitable AI model 1105. For example, these various deep learning techniques such as regression, classification, feature extraction, and the like. Any generated AI models may be iteratively tested to ensure they are not overfitted and sufficiently generalized for creating the comparison and list of probabilities in accordance with method of the invention.

In some embodiments, using a cross-validation method on the training process would optimize neural network hyperparameters to try to ensure that the neural network can sufficiently learn the distribution of all possible image types without overfitting to the training data. In some embodiments, after finalizing the neural network architecture, the neural network may be trained on all of the data available in the training image files.

In various embodiments, batch training may be used, and each batch may consist of multiple images, thirty-two for example, wherein each example image may be gray-scale, preferably 128*128 pixels although 256*256 pixels and other scaled may be used, without any preprocessing applied to it.

In some embodiments, the deep neural network parameters may be optimized using the Adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behaviour. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent overfitting and add more transitional invariance to the model. Therefore, in some embodiments, the training images may be augmented on-the-fly while training. In every mini-batch, each sample may be translated horizontally and vertically, rotated and/or zoomed, for example. The present invention is not intended to be limited to any one particular form of data augmentation, in training the AI model. As such, any mode of data augmentation which enhances the size and quality of the data set and applies random transformations which do not change the appropriateness of the label assignments may be employed, including but not limited to image flipping, rotation, translations, zooming, skewing, and elastic deformations.

Referring still to FIG. 11, after training has been completed, the sets of parameters stored in the storage memory may represent a trained neural network of a plurality of images of ROIs which identifies and segments boundaries of features with each ROI, in whole or part.

In order to assess the performance of AI model 1105, the stored model parameter values can be retrieved any time to perform image assessment through applying an image to the neural networks (shown as 1107) represented thereby. In some embodiments, the deep neural network may include various layers such as convolutional layers, pooling layers, and fully connected layers. In some embodiments, the final layers may include a softmax layer as an output layer having outputs which eventually would demonstrate respective determinations that an input set of pixels fall within a particular area above or below a feature boundary, in the training images. Accordingly, in some embodiments, the neural network may take at least one image as an input and output a binary mask indicating which pixels belong to the area above a feature boundary (or part thereof), e.g., the AI model classifies which area each pixel belongs to.

To increase the robustness of the AI model 1105, in some embodiments, a broad set of training data may be used at act 1104. For example, it is desired that ultrasound images of a plurality of different ROIs, across a plurality of anatomical regions in a body, in whole and a variety of parts thereof, from views including but not limited to coronal and/or transverse plane views, including views from different angles that combine any of a sagittal plane view, a coronal plane view, or a transverse plane view.

More specifically, training images 1102 and 1103 may be labeled with one or more features associated with/are hallmarks of a particular ROI, including key anatomical features therein. This may include identifying a variety of features visualized in the captured training image. In at least some embodiments, this data may be received from trainer/user input. For example, a trainer/user may label the features relevant for the application visualized in each training image.

The image labeling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper and accurate feature identification. For example, this can include training ultrasound images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, training ultrasound images 1102 and 1103 can include a graduation of training images ranging from images with just sufficient image quality to high image quality. In this manner, the machine learning model may be trained to identify features on training medical images that have varying levels of sufficient image quality for later interpretation and probability assessment.

Overall, the scope of the invention and accorded claims are not intended to be limited to any one particular process of training AI model 1105. Such examples are provided herein by way of example only. AI model 1105 may be trained by both supervised and unsupervised learning approaches although due to scalability, unsupervised learning approaches, which are well known in the art, are preferred. Other approaches may be employed to strengthen AI model 1105.

The image labelling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper and accurate feature identification. For example, this can include training ultrasound images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, training ultrasound images can include a graduation of training medical images ranging from images with just sufficient image quality to high image quality. In this manner, the machine learning model may be trained to identify features on training medical images that have varying levels of sufficient image quality for later interpretation and probability assessment.

Turning back to FIG. 11, once a satisfactory AI model 1105 is generated, the AI model 1105 may be deployed for execution on a neural network 1107 to identify and segment boundaries of features, in whole or part, within a ROI. Notably, the neural network 1107 is shown in FIG. 11 for illustration as a convolution neural network—with various nodes in the input layer, hidden layers, and output layers. However, in various embodiments, different arrangements of the neural network 1107 may be possible.

In various embodiments, prior to being processed for analysis as described herein, training ultrasound image frames may optionally be pre-processed in a manner analogous to the pre-processing act 103 in FIG. 1. (e.g., processing through a high contrast filter and/or scaling), to facilitate and improve accuracy in identifying and selecting boundaries of features, in whole or part.

The training images file may include an image identifier field for storing a unique identifier for identifying an image included in the file, a segmentation mask field for storing an identifier for specifying the to-be-trimmed area, and an image data field for storing information representing the image.

Referring again to FIG. 11, once a satisfactory AI model 1105 is generated, the AI model 1105 may be deployed for execution on a neural network 1107 to segment a single feature or two or more features, as described fully herein, new ultrasound images 1108. Notably, the neural network 1107 is shown in FIG. 11 for illustration as a convolution neural network—with various nodes in the input layer, hidden layers, and output layers. However, in various embodiments, different arrangements of the neural network 1107 may be possible.

In various embodiments, prior to being processed for feature segmentation, the new ultrasound images 1108 may optionally be pre-processed. This is shown in FIG. 11 with the pre-processing act 1106 in dotted outline. In some embodiments, these pre-processing acts 1106 may be analogous to the pre-processing acts 1101 performed on the training ultrasound frames 1102 and 1103 (e.g., processing through a high contrast filter and/or scaling), to better align the new ultrasound images 1108 with the training ultrasound image frames, and thereby facilitate improved accuracy in feature segmentation. For example, pre-processing an input image may help standardize the input image so that it matches the format (e.g., having generally the same dimensions and parameters) of the training ultrasound images 1102 and 1103 that the AI model 1105 is trained on.

In various embodiments, the new ultrasound images 1108 may be live images acquired by an ultrasound imaging system (e.g., the system discussed with respect to FIGS. 13 and 14 below). For example, the AI model 1105 may be deployed for execution on the scanner 1331 and/or the display device 1350 discussed in more detail below. Additionally, or alternatively, the AI model 1105 may be executed on stored (as opposed to new) ultrasound images 1109 that were previously acquired (e.g., as may be stored on a Picturing Archiving and Communication System (PACS)).

Whether the images are stored ultrasound images 1109 or new ultrasound images 1108, the AI model 1105 enables the neural network 1107 to properly segment a single feature or two or more features within a ROI imaged in the new/stored ultrasound imaging data and create a segmented/intermediary image 1110. As noted above, ultrasound frame 1102, which is marked as acceptable, comprises two segmented boundary features 1115a and 1116a, which are marked as correctly and at least adequality segmented. In new ultrasound images 1108, the regions sought to be segmented, correctly as noted as 1115b and 1116b such that, after processing through neural network 1107, segmented/intermediary image 1110 comprises two correctly segmented boundary features 1115d and 1116d. Likewise ultrasound images 1109, the regions sought to be segmented, correctly as noted as 1115c and 1116c such that, after processing through neural network 1107, segmented/intermediary image 1110 comprises two correctly segmented boundary features 1115d and 1116d.

FIG. 12 is flowchart diagram of the steps, generally indicated as 1200, for training the AI model of FIG. 11, according to an embodiment of the present invention. In some embodiments, method 1200 may be implemented as executable instructions in any appropriate combination of the imaging system 1330 (FIG. 13), for example, an external computing device connected to the imaging system 1330, in communication with the imaging system 1330, and so on. As one example, method 1200 may be implemented in non-transitory memory of a computing device, such as the controller (e.g., processor) of the imaging system 1330.

Referring still to FIG. 12, in step 1201, a training ultrasound image may be obtained. For example, a training ultrasound image may be acquired by the scanner 1331 (as shown in FIG. 13) transmitting and receiving ultrasound energy. The training ultrasound image may generally be a post-scan converted ultrasound image. While the method of FIG. 12 is described in relation to a single training ultrasound image, the method may also apply to the use of multiple training ultrasound images. While the method of FIG. 12 is described in relation to a post-scan ultrasound image, it is to be understood that pre-scan images, may be used, as described in U.S. patent application Ser. No. 17/187,851 filed Feb. 28, 2021, the entire contents of which are incorporated herein by reference.

Optionally, in step 1202 (as shown in dotted outline), the resolution of the training ultrasound image may be adjusted. For example, the resolution may be increased or decreased. The purpose of this may be to provide the labeler (e.g., a medical professional with relevant clinical expertise) with training ultrasound images that have a more standardized appearance. This may help to maintain a higher consistency with which the labeler identifies anatomical features in the training ultrasound images. Besides the resolution, other parameters of the training ultrasound image may also be adjusted such as input scaling, screen size, pixel size, aspect ratio, and the removal of dead space, as described above (including, for example, data augmentation and other pre-processing steps).

In step 1203, the training ultrasound image may be displayed on a display device, such as the display device 1350 discussed in more detail below in relation to FIG. 13. The labeler can then identify a particular anatomy in the training ultrasound image by, for example, tagging it with a name from a pull-down menu or by using other labeling techniques and modalities. The labeler then can mark the training ultrasound image around the particular anatomy that the labeler has identified in the training ultrasound image. In step 1204, the system that is used for the training may receive the identification of the anatomical feature(s) on the training ultrasound image. In step 1205, the system may generate, for example, from a labeler's marking inputs, identified boundaries of a feature or features in the training ultrasound frame. In step 1206, a boundary feature is segmented in order to, at step 1207, generate a labeled training image.

In various embodiments, steps may readily be interchanged with each other. For example, the generation of labeled confirmation at step 1207 may automatically proceed, without trainer intervention, using prior data which directs to the placement of feature boundaries.

Once the training ultrasound image has been segmented and labeled, the system may then remove, in step 1208, optionally, (as shown in dotted outline), regions of the labeled ultrasound data frame that are both outside the area of the identified boundary features and outside areas relevant for the AI model to recognize the particular anatomy within the ROI. For example, the labeled ultrasound data frame may be truncated at one or more sides. Truncation of some of the ultrasound data may allow the training of the AI model to proceed more quickly. There is provided a redirection at step 1209 to repeat steps 1201-1208 a plurality of times, for additional training images. At step 1210, AI model is trained. At step 1211, once training is completed, the AI model may be used to perform identifications and selections on an unseen dataset to validate its performance, such evaluation at step 1211 feeding data back to train the AI model at step 1210.

Figure 13:
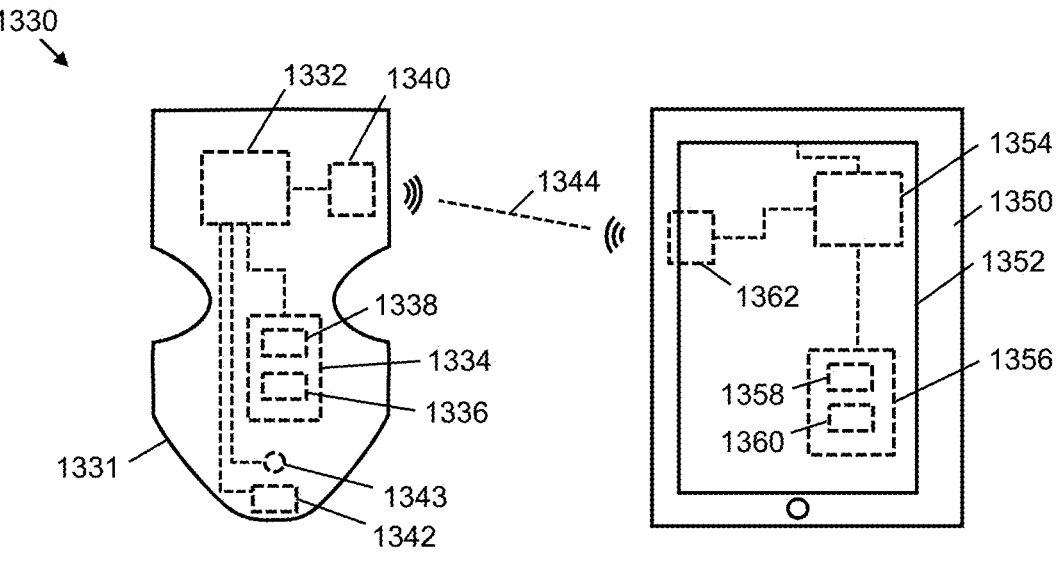
FIG. 13 is a schematic diagram of an ultrasound imaging system, according to an embodiment of the present invention.

Referring to FIG. 13, an exemplary system 1330 is shown for creating and displaying a visually distinct rendering of an ultrasound image, acquired from an ultrasound scanner. The system 1330 includes an ultrasound scanner 1331 with a processor 1332, which is connected to a non-transitory computer readable memory 1334 storing computer readable instructions 1336, which, when executed by the processor 1332, may cause the scanner 1331 to provide one or more of the functions of the system 1330. Such functions may be, for example, the acquisition of ultrasound data, the processing of ultrasound data, the scan conversion of ultrasound data, the transmission of ultrasound data or ultrasound frames to a display device 150, the detection of operator inputs to the ultrasound scanner 131, and/or the switching of the settings of the ultrasound scanner 131.

Also stored in the computer readable memory 1334 may be computer readable data 1338, which may be used by the processor 1332 in conjunction with the computer readable instructions 1336 to provide the functions of the system 1330. Computer readable data 1338 may include, for example, configuration settings for the scanner 1331, such as presets that instruct the processor 1332 how to collect and process the ultrasound data for a plurality of ROIs and how to acquire a series of ultrasound frames. The scanner 1331 may include an ultrasonic transducer 1342 that transmits and receives ultrasound energy in order to acquire ultrasound frames. The scanner 1331 may include a communications module 1340 connected to the processor 1332. In the illustrated example, the communications module 1340 may wirelessly transmit signals to and receive signals from the display device 1350 along wireless communication link 1344. The protocol used for communications between the scanner 1331 and the display device 1350 may be WiFi™ or Bluetooth™, for example, or any other suitable two-way radio communications protocol. In some embodiments, the scanner 1331 may operate as a WiFi™ hotspot, for example. Communication link 1344 may use any suitable wireless communications network connection. In some embodiments, the communication link between the scanner 1331 and the display device 1350 may be wired. For example, the scanner 1331 may be attached to a cord that may be pluggable into a physical port of the display device 1350.

In various embodiments, the display device 13350 may be, for example, a laptop computer, a tablet computer, a desktop computer, a smart phone, a smart watch, spectacles with a built-in display, a television, a bespoke display or any other display device that is capable of being communicably connected to the scanner 1331. The display device 1350 may host a screen 1352 and may include a processor 1354, which may be connected to a non-transitory computer readable memory 1356 storing computer readable instructions 1358, which, when executed by the processor 1354, cause the display device 1350 to provide one or more of the functions of the system 1330. Such functions may be, for example, the receiving of ultrasound data that may or may not be pre-processed; scan conversion of received ultrasound data into an ultrasound image; processing of ultrasound data in image data frames; the display of a user interface; the control of the scanner 1331; the display of an ultrasound image on the screen 1352; the processing of using the AI model, new ultrasound image to identify and segment boundaries of two or more features, in whole or part, on the new ultrasound image, creating two or more segmented boundary features; and applying a graphic onto the at least two segmented boundary features, thereby forming a graphic feature image; and/or the storage, application, reinforcing and/or training of AI model 1105. The screen 1352 may comprise a touch-sensitive display (e.g., touchscreen) that can detect a presence of a touch from the operator on screen 1352 and can also identify a location of the touch in screen 1352. The touch may be applied by, for example, at least one of an individual's hand, glove, stylus, or the like. As such, the touch-sensitive display may be used for example to toggle text on the graphic feature image on and off or to provide other inputs regarding the application of graphics to the segmented boundary features. The screen 1352 and/or any other user interface may also communicate audibly. The display device 1350 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory 1356 may be computer readable data 1360, which may be used by the processor 1354 in conjunction with the computer readable instructions 1358 to provide the functions of the system 1330. Computer readable data 1360 may include, for example, settings for the scanner 1331, such as presets for acquiring ultrasound data; settings for a user interface displayed on the screen 1352; and/or data for one or more AI models within the scope of the invention. Settings may also include any other data that is specific to the way that the scanner 1331 operates or that the display device 1350 operates. It can therefore be understood that the computer readable instructions and data used for controlling the system 1330 may be located either in the computer readable memory 1334 of the scanner 1331, the computer readable memory 1356 of the display device 1350, and/or both the computer readable memories 1334, 1356.

The display device 1350 may also include a communications module 1362 connected to the processor 1354 for facilitating communication with the scanner 1331. In the illustrated example, the communications module 1362 wirelessly transmits signals to and receives signals from the scanner 1331 on wireless communication link 1344. However, as noted, in some embodiments, the connection between scanner 1331 and display device 1350 may be wired.

Figure 14:
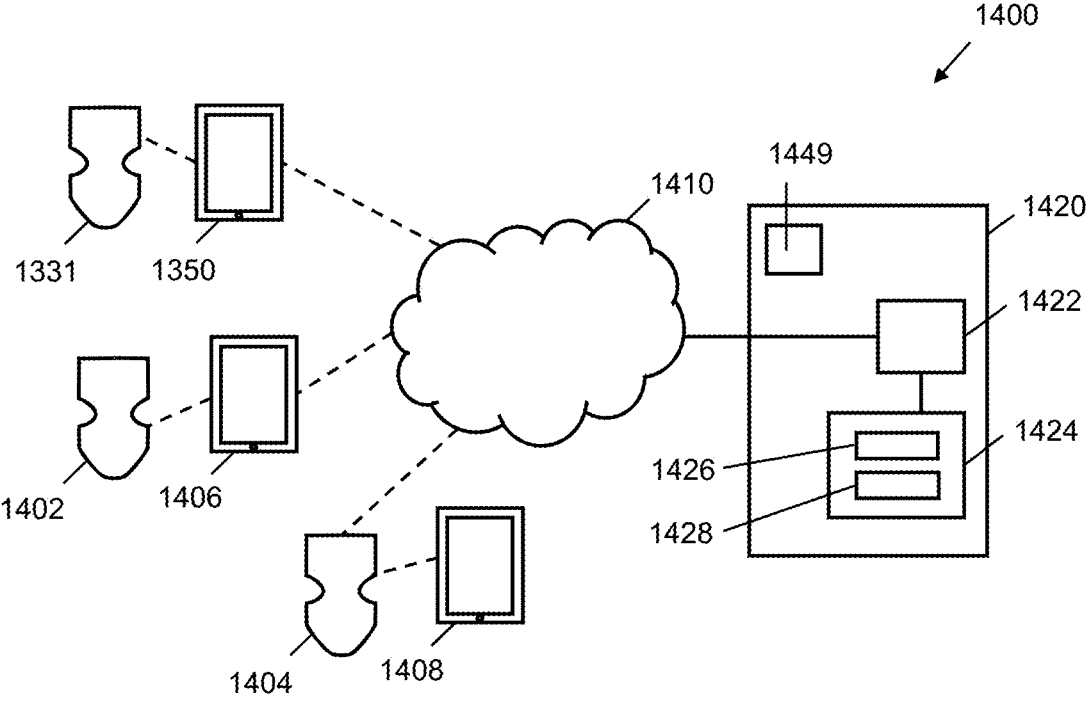
FIG. 14 is a schematic diagram of a system with multiple ultrasound scanners, according to an embodiment of the present invention.

Referring to FIG. 14, a system 1400 is shown in which there are multiple similar or different scanners 1401, 1402, 1404 connected to their corresponding display devices 1350, 1406, 1408 and either connected directly, or indirectly via the display devices, to a communications network 1410, such as the internet. The scanners 1331, 1402, 1404 may be connected onwards via the communications network 1410 to a server 1420. The server 1420 may include a processor 1422, which may be connected to a non-transitory computer readable memory 1424 storing computer readable instructions 1426, which, when executed by the processor 1422, cause the server 1420 to provide one or more of the functions of the system 1400. Such functions may be, for example, the receiving of ultrasound frames, the processing of ultrasound data in ultrasound frames, the control of the scanners 1331, 1402, 1404, the processing of using the AI model of new ultrasound images to identify and segment boundaries of two or more features, in whole or part, on the new ultrasound image, thereby creating two or more segmented boundary features; and applying a graphic onto the at least two segmented boundary features, thereby forming a graphic feature image; and/or machine learning activities related to one or more AI models 1105 (as discussed above in relation to FIGS. 1, 11 and 12).

Also stored in the computer readable memory 1424 may be computer readable data 1428, which may be used by the processor 1422 in conjunction with the computer readable instructions 1426 to provide the functions of the system 1400. Computer readable data 1428 may include, for example, settings for the scanners 1331, 1402, 1404 such as preset parameters for acquiring ultrasound data, settings for user interfaces displayed on the display devices 1350, 1406, 1408, and data for one or more AI models 1105. Settings may also include any other data that is specific to the way that the scanners 1331, 1402, 1404 operate or that the display devices 1350, 1406, 1408 operate.

It can therefore be understood that the computer readable instructions and data used for controlling the system 1400 may be located either in the computer readable memory of the scanners 1331, 1402, 1404, the computer readable memory of the display devices 1350, 1406, 1408, the computer readable memory 1424 of the server 1420, or any combination of the foregoing locations.

As noted above, even though the scanners 1331, 1402, 1404 may be different, each ultrasound frame acquired may be used by the AI model 1105 for training purposes. Likewise, ultrasound frames acquired by the individual scanners 1331, 1402, 1404 may all be processed against the AI model 1105 for reinforcement of the AI model 1105. In some embodiments, the AI models 1105 present in the display devices 1350, 1406, 1408 may be updated from time to time from an AI model 1105 present in the server 1420, where the AI model present in the server is continually trained using ultrasound frames of additional data acquired by multiple scanners 1331, 1402, 1404.

Further to the discussion above with respect to FIGS. 3 and 4, FIGS. 17A, 17B and 17C are illustrative of changes to graphics, on graphic feature images, as a consequence of movement or motion and by tracking displacement of at least one aspect of the graphic feature image using a tracking algorithm, to direct adjustments to the graphic feature image within segmented boundary feature/features. As such, FIGS. 17A-17C represent visual discernment of the dynamic motion of a graphic feature image, in this case by movement of ultrasound scanner (1708, 1708b and 1708c) to a left direction, over patient skin (1710/1710b/1710c), as indicated by the directional arrow in FIG. 17B. A marker on the patient skin, shown as a flower tattoo (1712, 1712b, 1712c) provides a visual cue that the scanner is moving, by way of its location being to the left of the scanner in FIG. 17A, just to the right of the scanner in FIG. 17B and then not visible in FIG. 17C (off frame). Activation/scanning mode is depicted in the figures with ultrasonic waves 1709, 1709b and 1709c under the patient skin and wireless communication between the ultrasound scanner and display device is depicted by universal wireless signal (1730, 1730b and 1730c). Displays device 1701 offers a screen interface for viewing the sequential ultrasound images which have been acquired, segmented and then applied with graphics, in accordance with the embodiments of the present invention. Exemplary graphic feature images (1702, 1704 and 1706) comprise top layer (1714, 1714b and 1714c) and bottom layer (1716, 1716b and 1716c). Bottom layer comprises one large blue circle 1718 and a plurality of smaller black circles 1720, in FIG. 17A.

As scanner 1708 moves to the left, a working, transitional graphic feature image 1704 illustrates such movement by the transitional distortion and blurring of large blue circle 1718b and a plurality of smaller black circles 1720b, such movement enabled by tracking displacement of at least one aspect of the graphic feature image using a tracking algorithm, to direct adjustments to the graphic feature image within segmented boundary feature/features. Finally, such motion tracking results in the display of an updated graphic feature image 1706, wherein one large blue circle 1718c and the plurality of smaller black circles 1720c are non-distorted, clear and shifted to the right, as compared to 1702 (pre-movement). In this way, graphics are realistically applied and updated to displayed graphic feature images; and the appearance of the displayed graphic can give the visual effect of movement that corresponds to actual movement (e.g., either of the probe or the underlying tissue).

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the use of the masculine can refer to masculine, feminine or both;

where numerical values are given, they are specified to the nearest significant figure;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

The term "B-mode" refers to the brightness mode of an ultrasound scanner, in which an array of transducers simultaneously scans a plane through the body that can be viewed as a two-dimensional image on screen. This 2D ultrasound image display is composed of bright dots representing ultrasound echoes wherein the brightness of each dot is determined by the amplitude of the returned echo signal.

The term "module" can refer to any component in this invention and to any or all of the features of the invention without limitation. A module may be a software, firmware or hardware module, and may be located, for example, in the ultrasound scanner, a display device or a server.

Embodiments of the invention may be implemented using specifically designed hardware, configurable hardware, programmable data processors configured by the provision of software (which may optionally comprise "firmware") capable of executing on the data processors, special purpose computers or data processors that are specifically pro-grammed, configured, or constructed to perform one or more steps in a method as explained in detail herein and/or combinations of two or more of these. Examples of specifi-cally designed hardware are: logic circuits, application-specific integrated circuits ("ASICs"), large scale integrated circuits ("LSIs"), very large scale integrated circuits ("VL-SIs"), and the like. Examples of configurable hardware are: one or more programmable logic devices such as program-mable array logic ("PALs"), programmable logic arrays ("PLAs"), and field programmable gate arrays ("FPGAs"). Examples of programmable data processors are: micropro-cessors, digital signal processors ("DSPs"), embedded pro-cessors, graphics processors, math co-processors, general purpose computers, server computers, cloud computers, mainframe computers, computer workstations, and the like. For example, one or more data processors in a control circuit for a device may implement methods as described herein by executing software instructions in a program memory acces-sible to the processors.

For example, while processes or blocks are presented in a given order herein, alternative examples may perform routines having steps, or employ systems having blocks, in a different order, and some processes or blocks may be deleted, moved, added, subdivided, combined, and/or modi-fied to provide alternative or sub combinations. Each of these processes or blocks may be implemented in a variety of different ways. Also, while processes or blocks are at times shown as being performed in series, these processes or blocks may instead be performed in parallel or may be performed at different times.

The invention may also be provided in the form of a program product. The program product may comprise any non-transitory medium which carries a set of computer-readable instructions which, when executed by a data pro-cessor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be com-pressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodi-ments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, ele-ments and/or acts; mixing and matching of features, ele-ments and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112 (f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodi-ments set forth in the examples but should be given the broadest interpretation consistent with the description as a whole.

CLAIM SUPPORT

In a first broad aspect of the present disclosure, there is provided a method of creating and displaying a visually distinct rendering of an ultrasound image, acquired from an ultrasound scanner, the method comprising: displaying, on a screen that is communicatively connected to the ultrasound scanner, an ultrasound image feed comprising ultrasound image frames; deploying an AI model to execute on a computing device communicably connected to the ultra-sound scanner, wherein the AI model is trained so that when the AI model is deployed, the computing device identifies and segments boundaries of features, in whole or part; acquiring, at the computing device, a new ultrasound image during ultrasound scanning; processing, using the AI model, the new ultrasound image to identify and segment bound-aries of two or more features, in whole or part, on the new ultrasound image, thereby creating two or more segmented boundary features; applying a graphic onto the at least two segmented boundary features, thereby forming a graphic feature image; and generating an output image, on the screen, comprising the graphic feature image.

In a further broad aspect of the present disclosure, there is provided a method of creating and displaying a visually distinct rendering of an ultrasound image, acquired from an ultrasound scanner, the method comprising: displaying, on a screen that is communicatively connected to the ultrasound scanner, an ultrasound image feed comprising ultrasound image frames; deploying an AI model to execute on a computing device communicably connected to the ultra-sound scanner, wherein the AI model is trained so that when the AI model is deployed, the computing device identifies and segments boundaries of features, in whole or part; acquiring, at the computing device, a new ultrasound image during ultrasound scanning; processing, using the AI model, the new ultrasound image to identify and segment bound-aries of at least one feature, in whole or part, on the new ultrasound image, thereby creating at least one segmented boundary feature; applying a graphic onto the at least one segmented boundary feature, thereby forming a graphic feature image; and generating an output image, on the screen, comprising the graphic feature image.

In some embodiments, a different graphic is applied to each of the at least two segmented boundary features to form the graphic feature image.

In some embodiments, an AI model identifies and segments more than two segmented boundary features, within the new ultrasound image, and a different graphic is applied to each of the more than two segmented boundary features to form the graphic feature image.

In some embodiments, a graphic is applied in real time, during new ultrasound image acquisition.

In some embodiments, there is additionally provided a step of tracking displacement of at least one aspect of the graphic feature image using a tracking algorithm, to direct adjustments to the graphic feature image within the segmented boundary features.

In some embodiments, adjustments made to the segmented boundary features or segmented boundary feature creates a visual of dynamic motion of the graphic feature image.

In some embodiments, there is additionally provided the steps of tracking a motion of one or more of an annotation and artifact associated with at the segmented boundary feature, such one or more of an annotation and artifact being associated with a first location of the segmented boundary feature on a first image; capturing an adjustment of the one or more of an annotation or artifact on a second image, the adjustment being indicative of a second location of the one or more of an annotation or artifact; adjusting a graphic on the segmented boundary feature using a positional difference in location of the one or more of an annotation and artifact, between the first location and the second location; and generating an updated graphic feature image which creates an illusion of applying movement to the graphic on the segmented boundary feature.

In some embodiments, an artifact is a speckle artifact.

In some embodiments, a graphic is any visual representation selected from the group consisting of color, hue, contrast, shading, brightness, patterns, animation, line art, symbols, geometric designs, photorealistic designs, artistic designs, bitmap graphics, and vector graphics.

In some embodiments, a new ultrasound image is one or a combination of a live acquired ultrasound image and a stored, previously acquired ultrasound image.

In some embodiments, an AI model is trained with a plurality of training ultrasound images comprising labelled segmented boundaries of one or more features, which are, one of: i) generated by one of a manual or semi-automatic means; or ii) tagged from an identifier menu by one of a manual, semi-automatic means or fully automatic means.

In some embodiments, an AI model is trained with one or more of the following: i) supervised learning; ii) unsupervised learning; iii) previously labelled ultrasound image datasets; and iv) cloud stored data.

In some embodiments, a feature is selected from the group consisting of an organ, a portion of an organ, a boundary of an organ, a muscle, a boundary of a muscle, a blood vessel, a boundary of a blood vessel, a nerve, a boundary of a nerve, a fat layer, epithelium, bodily fluid, a tumor, and a cyst.

In a further broad aspect of the present disclosure, there is provided a system for generating and displaying a visually distinct rendering of an ultrasound image comprising: an ultrasound scanner configured to acquire a new ultrasound image frame; a computing device communicably connected to the ultrasound scanner and configured to: process the new ultrasound image frame against an artificial intelligence model to identify and segment boundaries of two or more features, in whole or part, on the new ultrasound image frame, thereby creating two or more segmented boundary features; apply a graphic onto the at least two segmented boundary features, thereby forming a graphic feature image;

generate an output image comprising the graphic feature image; and a display device configured to: display the output image comprising the graphic feature image.

In a further broad aspect of the present disclosure, there is provided a system for generating and displaying a visually distinct rendering of an ultrasound image comprising: an ultrasound scanner configured to acquire a new ultrasound image frame; a computing device communicably connected to the ultrasound scanner and configured to: process the new ultrasound image frame against an artificial intelligence model to identify and segment boundaries of at least one feature, in whole or part, on the new ultrasound image frame, thereby creating at least one segmented boundary feature; apply a graphic onto the at least one segmented boundary feature, thereby forming a graphic feature image; generate an output image comprising the graphic feature image; and a display device configured to: display the output image comprising the graphic feature image.

In some embodiments, a different graphic is applied to i) a single segmented boundary feature or ii) each of at least two segmented boundary features to form the graphic feature image.

In some embodiments, an AI model identifies and segments each of at least two segmented boundary features, within a new ultrasound image, and a different graphic is applied to each of the more than two segmented boundary features to form the graphic feature image.

In some embodiments, a computing device additionally tracks displacement of at least one aspect of the graphic feature image using a tracking algorithm, to direct adjustments to the graphic feature image within the segmented boundary features.

In some embodiments, adjustments to the segmented boundary features creates a visual of dynamic motion of the graphic feature image.

In some embodiments, a display device additionally displays, along with graphic feature image, at least one of: i) the new ultrasound image frame; and ii) an image frame showing the i) a single segmented boundary features; and/or ii) at least two segmented boundary features.

In a further broad aspect of the present disclosure, there is provided a computer-readable media storing computer-readable instructions, which, when executed by a processor cause the processor to: process a new ultrasound image frame against an artificial intelligence model to identify and segment boundaries of two or more features, in whole or part, on the new ultrasound image frame, thereby creating two or more segmented boundary features; apply a graphic onto the at least two segmented boundary features, thereby forming a graphic feature image; and generate and display an output image comprising the graphic feature image.

In a further broad aspect of the present disclosure, there is provided a computer-readable media storing computer-readable instructions, which, when executed by a processor cause the processor to: process a new ultrasound image frame against an artificial intelligence model to identify and segment boundaries of at least one feature, in whole or part, on the new ultrasound image frame, thereby creating at least one segmented boundary feature; apply a graphic onto the at least one segmented boundary feature, thereby forming a graphic feature image; and generate and display an output image comprising the graphic feature image.

What is claimed is:

1. A method of creating and displaying a visually distinct rendering of an ultrasound image, acquired from an ultrasound scanner, the method comprising:

displaying, on a screen that is communicatively connected to the ultrasound scanner, an ultrasound image feed comprising ultrasound image frames;

deploying an AI model to execute on a computing device communicably connected to the ultrasound scanner, wherein the AI model is trained so that when the AI model is deployed, the computing device identifies and segments boundaries of a feature or features, in whole or part;

acquiring, at the computing device, a new ultrasound image during ultrasound scanning;

processing, using the AI model, the new ultrasound image to identify and segment boundaries of two or more features, in whole or part, on the new ultrasound image, thereby creating two or more segmented boundary features;

applying at least two graphics respectively, onto the at least two segmented boundary features, wherein the at least two graphics substantially fill within the boundaries of the at least two segmented boundary features, thereby forming a graphic feature image; and generating an output image, on the screen, comprising the graphic feature image.

2. The method of claim 1 wherein each of the at least two graphics is a different graphic which is applied, respectively, to each of the at least two segmented boundary features to form the graphic feature image.

3. The method of claim 1 wherein the AI model identifies and segments more than two segmented boundary features, within the new ultrasound image, and a different graphic is applied to each of the more than two segmented boundary features to form the graphic feature image.

4. The method of claim 1 wherein the at least two graphics are applied in real time, during new ultrasound image acquisition.

5. The method of claim 1 additionally comprising a step of tracking displacement of at least one aspect of the graphic feature image using a tracking algorithm, to direct adjustments to the graphic feature image within the segmented boundary features.

6. The method of claim 5 wherein adjustments to the segmented boundary features creates a visual of dynamic motion of the graphic feature image.

7. The method of claim 1 additionally comprising the steps of tracking a motion of one or more of an annotation and artifact associated with at the segmented boundary feature, such one or more of an annotation and artifact being associated with a first location of the segmented boundary feature on a first image; capturing an adjustment of the one or more of an annotation or artifact on a second image, the adjustment being indicative of a second location of the one or more of an annotation or artifact; adjusting a graphic on the segmented boundary feature using a positional difference in location of the one or more of an annotation and artifact, between the first location and the second location; and generating an updated graphic feature image which creates an illusion of applying movement to the graphic on the segmented boundary feature.

8. The method of claim 7 wherein the artifact is a speckle artifact.

9. The method of claim 1 wherein the at least two graphics is any visual representation selected from the group consisting of color, hue, contrast, shading, brightness, patterns, animation, line art, symbols, geometric designs, photorealistic designs, artistic designs, bitmap graphics, and vector graphics.

10. The method of claim 1 wherein the new ultrasound image is one or a combination of a live acquired ultrasound image and a stored, previously acquired ultrasound image.

11. The method of claim 1 wherein the AI model is trained with a plurality of training ultrasound images comprising labelled segmented boundaries of one or more features, which are, one of: i) generated by one of a manual or semi automatic means; or ii) tagged from an identifier menu by one of a manual, semi automatic means or fully automatic means.

12. The method of claim 1 comprising training the AI model with one or more of the following: i) supervised learning; ii) unsupervised learning; iii) previously labelled ultrasound image datasets; and iv) cloud stored data.

13. The method of claim 1 wherein the feature is selected from the group consisting of an organ, a portion of an organ, a boundary of an organ, a muscle, a boundary of a muscle, a blood vessel, a boundary of a blood vessel, a nerve, a boundary of a nerve, a fat layer, epithelium, bodily fluid, a tumor, and a cyst.

14. A system for generating and displaying a visually distinct rendering of an ultrasound image comprising:

an ultrasound scanner configured to acquire a new ultrasound image frame;

a computing device communicably connected to the ultrasound scanner and configured to:

process the new ultrasound image frame against an artificial intelligence model to identify and segment boundaries of two or more features, in whole or part, on the new ultrasound image frame, thereby creating two or more segmented boundary features;

apply at least two graphics, respectively, onto the at least two segmented boundary features, wherein the at least two graphics substantially fill within the boundaries of the at least two segmented boundary features, thereby forming a graphic feature image;

generate an output image comprising the graphic feature image; and a display device configured to:

display the output image comprising the graphic feature image.

15. The system of claim 14 wherein each of the at least two graphics is a different graphic which is applied, respectively, to each of the at least two segmented boundary features to form the graphic feature image.

16. The system of claim 14 wherein the AI model identifies and segments more than two segmented boundary features, within the new ultrasound image, and a different graphic is applied to each of the more than two segmented boundary features to form the graphic feature image.

17. The system of claim 14 wherein the computing device additionally tracks displacement of at least one aspect of the graphic feature image using a tracking algorithm, to direct adjustments to the graphic feature image within the segmented boundary features.

18. The system of claim 17 wherein adjustments to the segmented boundary features creates a visual of dynamic motion of the graphic feature image.

19. The system of claim 14 wherein the display device additionally displays, along with graphic feature image, at least one of: i) the new ultrasound image frame; and ii) an image frame showing the at least two segmented boundary features.

20. A non-transitory computer-readable media storing computer-readable instructions, which, when executed by a processor cause the processor to:

display on a screen that is communicatively connected to an ultrasound scanner, an ultrasound image feed comprising ultrasound image frames;

deploy an AI model to execute on a computing device communicably connected to the ultrasound scanner, wherein the AI model is trained so that when the AI model is deployed, the computing device identifies and segments boundaries of a feature or features, in whole or part;

acquire, at the computing device a new ultrasound image during ultrasound scanning;

process the new ultrasound image frame against the AI model to identify and segment boundaries of two or more features, in whole or part, on the new ultrasound image frame, thereby creating two or more segmented boundary features;

apply at least two graphics, respectively, onto the at least two segmented boundary features, wherein the at least two graphics substantially fill within the boundaries of the at least two segmented boundary features, thereby forming a graphic feature image; and generate and display an output image comprising the graphic feature image.

\* \* \* \* \*